United States Patent
Rogers et al.

(10) Patent No.: US 6,740,029 B2
(45) Date of Patent: *May 25, 2004

(54) DEVICE AND METHOD FOR ISOLATING A SURFACE OF A BEATING HEART DURING SURGERY

(75) Inventors: Danny Carpenter Rogers, Athens, TX (US); Samuel Lynn Austin, Eustace, TX (US); Albert Davis, Richardson, TX (US); Charles R. Keyes, Jr., Athens, TX (US); Clyde Baker, South Jordan, UT (US)

(73) Assignee: Chase Medical, L.P., Richardson, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/235,320

(22) Filed: Sep. 5, 2002

(65) Prior Publication Data

US 2003/0009081 A1 Jan. 9, 2003

Related U.S. Application Data

(63) Continuation of application No. 09/632,430, filed on Aug. 4, 2000, which is a continuation-in-part of application No. 09/376,538, filed on Aug. 18, 1995, now Pat. No. 6,258,023.
(60) Provisional application No. 60/143,023, filed on Jul. 8, 1999.

(51) Int. Cl.[7] .................................................. A61F 2/00

(52) U.S. Cl. ........................................................ 600/37

(58) Field of Search .......................... 600/37, 207, 206, 600/205, 213, 228, 229, 231, 217, 16, 17, 219; 604/28, 30; 128/898, 897; 606/150, 155, 148, 205, 207; 607/126, 125; 204/613, 614

(56) References Cited

U.S. PATENT DOCUMENTS 452,131 A 5/1891 Haughawout (List continued on next page.)

FOREIGN PATENT DOCUMENTS

BR 9301980 10/1993

(List continued on next page.)

OTHER PUBLICATIONS

"To Use or Not to Use the Pump Oxygenator in Coronary Bypass Operation", Ankeney MD, The Annals of Thoracic Surgery, vol. 19, No. 1, Jan. 1975, pp. 108–109.

(List continued on next page.)

Primary Examiner—Eric F. Winakur
Assistant Examiner—Nikita R. Veniaminov
(74) Attorney, Agent, or Firm—Meyertons, Hood, Kivlin, Kowert & Goetzel, P.C.; Eric B. Meyertons

(57) ABSTRACT

Disclosed is a device for isolating a cardiac surgical site. The device comprises a first finger having a clinging accessory for attaching the first finger to a heart, a second finger having a clinging accessory for attaching the second finger to the heart, a first joint disposed on the first finger so that the first finger may rotate on a surface of the heart such that said rotation stretches a surgical site, a first stopper disposed on the first finger for preventing undesired rotation of the first finger to isolate the surgical site, and a link for coupling the first finger to the second finger. Several embodiments of the fingers and clinging accessories are disclosed. A guard is provided to protect sutures from the clinging accessory. The guard is equipped with a sprayer to wash the surgical site. Also disclosed is a method of isolating a cardiac surgical site. The method comprises the steps of disposing a first finder on a heart, clinging the first finger to the heart surface, disposing a second finger on a heart, clinging the second finger to the heart surface, and then rotating the first finger for achieving selective isolation of the heart surface.

27 Claims, 9 Drawing Sheets

U.S. PATENT DOCUMENTS

| | | |
|---|---|---|
| 497,064 A | 5/1893 | Van Meter |
| 810,675 A | 1/1906 | Richter |
| 1,157,202 A | 10/1915 | Bates et al. |
| 1,400,616 A | 12/1921 | McCrory et al. |
| 1,706,500 A | 3/1929 | Smith |
| 1,707,689 A | 4/1929 | Sloan |
| 1,839,726 A | 1/1932 | Arnold |
| 1,919,120 A | 7/1933 | O'Connor et al. |
| 1,963,173 A | 6/1934 | Morin |
| 2,053,868 A | 9/1936 | Grosso |
| 2,082,782 A | 6/1937 | Allen |
| 2,296,793 A | 9/1942 | Kirschbaum |
| 2,384,304 A | 9/1945 | Helfrick |
| 2,473,266 A | 6/1949 | Wexler |
| 2,590,527 A | 3/1952 | Fluck |
| 2,594,086 A | 4/1952 | Smith |
| 2,623,517 A | 12/1952 | Barlow et al. |
| 2,693,795 A | 11/1954 | Grieshaber |
| 2,701,562 A | 2/1955 | Michael et al. |
| 2,863,444 A | 12/1958 | Winsten |
| 3,070,088 A | 12/1962 | Brahos |
| 3,129,706 A | 4/1964 | Reynolds, Jr. |
| 3,168,093 A | 2/1965 | Gauthier |
| 3,384,077 A | 5/1968 | Gauthier |
| 3,463,144 A | 8/1969 | Hammond |
| 3,503,399 A | 3/1970 | Fogarty et al. |
| 3,509,873 A | 5/1970 | Karlin et al. |
| 3,515,129 A | 6/1970 | Truhan |
| 3,522,799 A | 8/1970 | Gauthier |
| 3,720,433 A | 3/1973 | Rosfelder |
| 3,724,449 A | 4/1973 | Gauthier |
| 3,749,088 A | 7/1973 | Kohlmann |
| 3,783,873 A | 1/1974 | Jacobs |
| 3,858,578 A | 1/1975 | Milo |
| 3,882,855 A | 5/1975 | Schulte et al. |
| 3,965,890 A | 6/1976 | Gauthier |
| 3,983,863 A | 10/1976 | Janke et al. |
| 3,998,217 A | 12/1976 | Trumbull et al. |
| 4,010,741 A | 3/1977 | Gauthier |
| 4,048,987 A | 9/1977 | Hurson |
| 4,049,000 A | 9/1977 | Williams |
| 4,052,980 A | 10/1977 | Grams et al. |
| 4,190,042 A | 2/1980 | Sinnreich |
| 4,217,890 A | 8/1980 | Owens |
| 4,226,228 A | 10/1980 | Shin et al. |
| 4,245,638 A | 1/1981 | Lebeck et al. |
| 4,254,763 A | 3/1981 | McCready et al. |
| 4,306,561 A | 12/1981 | de Medinaceli |
| 4,337,762 A | 7/1982 | Gauthier |
| 4,355,631 A | 10/1982 | LeVahn |
| 4,366,819 A | 1/1983 | Kaster |
| 4,368,736 A | 1/1983 | Kaster |
| 4,421,107 A | 12/1983 | Estes et al. |
| 4,424,724 A | 1/1984 | Bookwalter et al. |
| 4,428,368 A | 1/1984 | Torii |
| 4,430,991 A | 2/1984 | Darnell |
| 4,434,791 A | 3/1984 | Darnell |
| 4,454,888 A * | 6/1984 | Gold .......................... 607/125 |
| 4,457,300 A | 7/1984 | Budde |
| 4,461,284 A | 7/1984 | Fackler |
| 4,492,229 A | 1/1985 | Grunwald |
| 4,562,832 A | 1/1986 | Wilder et al. |
| 4,616,632 A | 10/1986 | Wigoda |
| 4,617,916 A | 10/1986 | LeVahn et al. |
| 4,622,955 A | 11/1986 | Fakhrai |
| 4,627,421 A | 12/1986 | Symbas et al. |
| 4,635,636 A | 1/1987 | Goldstein |
| 4,637,377 A | 1/1987 | Loop |
| 4,646,747 A | 3/1987 | Lundback |
| 4,688,570 A | 8/1987 | Kramer et al. |
| 4,702,230 A | 10/1987 | Pelta |
| 4,716,888 A * | 1/1988 | Wesner ....................... 607/126 |
| 4,718,151 A | 1/1988 | LeVahn et al. |
| 4,718,418 A | 1/1988 | L'Esperance, Jr. |
| 4,726,356 A | 2/1988 | Santilli et al. |
| 4,726,358 A | 2/1988 | Brady |
| 4,744,363 A | 5/1988 | Hasson |
| 4,747,395 A | 5/1988 | Brief |
| 4,754,746 A | 7/1988 | Cox |
| 4,765,311 A | 8/1988 | Kulik et al. |
| 4,796,846 A | 1/1989 | Meier et al. |
| 4,813,401 A | 3/1989 | Grieshaber |
| 4,829,985 A | 5/1989 | Couetil |
| 4,834,090 A | 5/1989 | Moore |
| 4,852,552 A | 8/1989 | Chaux |
| 4,854,318 A | 8/1989 | Solem et al. |
| 4,865,019 A | 9/1989 | Phillips |
| 4,884,559 A | 12/1989 | Collins |
| 4,925,443 A | 5/1990 | Heilman et al. |
| 4,932,395 A | 6/1990 | Mehdizadeh |
| 4,945,897 A | 8/1990 | Greenstein et al. |
| 4,946,463 A | 8/1990 | Wright |
| 4,949,707 A | 8/1990 | LeVahn et al. |
| 4,955,896 A | 9/1990 | Freeman |
| 4,962,758 A | 10/1990 | Lasner et al. |
| 4,971,037 A | 11/1990 | Pelta |
| 4,973,300 A | 11/1990 | Wright |
| 4,989,587 A | 2/1991 | Farley |
| 4,993,862 A | 2/1991 | Pelta |
| 5,000,163 A | 3/1991 | Ray et al. |
| 5,025,779 A | 6/1991 | Bugge |
| 5,037,428 A | 8/1991 | Picha et al. |
| 5,052,373 A | 10/1991 | Michelson |
| 5,052,374 A | 10/1991 | Alvarez-Jacinto |
| 5,053,041 A | 10/1991 | Ansari et al. |
| 5,067,477 A | 11/1991 | Santangelo |
| 5,080,088 A | 1/1992 | LeVahn |
| 5,088,472 A | 2/1992 | Fakhrai |
| 5,098,369 A | 3/1992 | Heilman et al. |
| 5,119,804 A | 6/1992 | Anstadt |
| 5,131,905 A | 7/1992 | Grooters |
| 5,133,724 A | 7/1992 | Wilson, Jr. et al. |
| 5,147,371 A | 9/1992 | Washington et al. |
| 5,150,706 A | 9/1992 | Cox et al. |
| 5,152,777 A | 10/1992 | Goldberg et al. |
| 5,159,921 A | 11/1992 | Hoover |
| RE34,150 E | 12/1992 | Santilli et al. |
| 5,167,223 A | 12/1992 | Koros et al. |
| 5,171,254 A | 12/1992 | Sher |
| 5,195,506 A | 3/1993 | Hulfish |
| 5,197,948 A | 3/1993 | Ghodsian |
| 5,231,974 A | 8/1993 | Giglio et al. |
| 5,256,132 A | 10/1993 | Snyders |
| 5,284,130 A | 2/1994 | Ratliff |
| 5,293,863 A | 3/1994 | Zhu et al. |
| 5,299,563 A | 4/1994 | Seton |
| 5,300,087 A | 4/1994 | Knoepfler |
| 5,306,234 A | 4/1994 | Johnson |
| 5,318,579 A | 6/1994 | Chow |
| 5,336,252 A | 8/1994 | Cohen |
| 5,363,841 A | 11/1994 | Coker |
| 5,365,921 A | 11/1994 | Bookwalter et al. |
| 5,372,124 A | 12/1994 | Takayama et al. |
| 5,374,277 A | 12/1994 | Hassler |
| 5,375,481 A | 12/1994 | Cabrera et al. |
| 5,381,788 A | 1/1995 | Matula et al. |
| 5,383,840 A | 1/1995 | Heilman et al. |
| 5,400,772 A | 3/1995 | LeVahn et al. |
| 5,400,774 A | 3/1995 | Villalta et al. |
| 5,405,360 A | 4/1995 | Tovey |
| 5,425,705 A | 6/1995 | Evard et al. |

| Patent | Date | Inventor |
|---|---|---|
| 5,437,651 A | 8/1995 | Todd et al. |
| 5,447,515 A | 9/1995 | Robicsek |
| 5,452,733 A | 9/1995 | Sterman et al. |
| 5,453,078 A | 9/1995 | Valentine et al. |
| 5,467,763 A | 11/1995 | McMahon et al. |
| 5,476,479 A | 12/1995 | Green et al. |
| 5,498,256 A | 3/1996 | Furnish |
| 5,503,617 A | 4/1996 | Jako |
| 5,509,890 A | 4/1996 | Kazama |
| 5,512,037 A | 4/1996 | Russell et al. |
| 5,514,075 A | 5/1996 | Moll et al. |
| 5,514,076 A | 5/1996 | Ley |
| 5,520,610 A | 5/1996 | Giglio et al. |
| 5,527,319 A | 6/1996 | Green et al. |
| 5,529,571 A | 6/1996 | Daniel |
| 5,536,251 A | 7/1996 | Evard et al. |
| 5,545,123 A | 8/1996 | Ortiz et al. |
| 5,547,458 A | 8/1996 | Ortiz et al. |
| 5,558,621 A | 9/1996 | Heil |
| 5,569,274 A | 10/1996 | Rapacki et al. |
| 5,571,074 A | 11/1996 | Buckman, Jr. et al. |
| 5,573,496 A | 11/1996 | McPherson et al. |
| 5,582,580 A | 12/1996 | Buckman, Jr. et al. |
| 5,613,937 A | 3/1997 | Garrison et al. |
| 5,651,378 A | 7/1997 | Matheny et al. |
| 5,667,480 A | 9/1997 | Knight et al. |
| 5,713,951 A | 2/1998 | Garrison et al. |
| 5,720,754 A | 2/1998 | Middleman et al. |
| 5,727,569 A | 3/1998 | Benetti et al. |
| 5,728,151 A | 3/1998 | Garrison et al. |
| 5,730,757 A | 3/1998 | Benetti et al. |
| 5,735,290 A | 4/1998 | Sterman et al. |
| 5,741,210 A | 4/1998 | Dobrovolny |
| 5,749,892 A | 5/1998 | Vierra et al. |
| 5,755,660 A | 5/1998 | Tyagi |
| 5,766,151 A | 6/1998 | Valley et al. |
| 5,772,583 A | 6/1998 | Wright et al. |
| 5,782,746 A | 7/1998 | Wright |
| 5,782,753 A | 7/1998 | DeFonzo et al. |
| 5,788,630 A | 8/1998 | Furnish |
| 5,795,291 A | 8/1998 | Koros et al. |
| 5,799,661 A | 9/1998 | Boyd et al. |
| 5,807,243 A | 9/1998 | Vierra et al. |
| 5,836,311 A | 11/1998 | Borst et al. |
| 5,846,187 A | 12/1998 | Wells et al. |
| 5,846,191 A | 12/1998 | Wells et al. |
| 5,846,193 A | 12/1998 | Wright |
| 5,846,194 A | 12/1998 | Wasson et al. |
| 5,865,730 A | 2/1999 | Fox et al. |
| 5,865,731 A | 2/1999 | Lenox et al. |
| 5,868,770 A | 2/1999 | Rygaard |
| 5,875,782 A | 3/1999 | Ferrari et al. |
| 5,876,332 A | 3/1999 | Looney |
| 5,879,291 A | 3/1999 | Kolata et al. |
| 5,882,299 A | 3/1999 | Rastegar et al. |
| 5,885,271 A | 3/1999 | Hamilton et al. |
| 5,888,247 A | 3/1999 | Benetti |
| 5,891,017 A | 4/1999 | Swindle et al. |
| 5,893,831 A | 4/1999 | Koros et al. |
| 5,894,843 A | 4/1999 | Benetti et al. |
| 5,897,490 A | 4/1999 | Fox et al. |
| 5,906,607 A | 5/1999 | Taylor et al. |
| 5,908,382 A | 6/1999 | Koros et al. |
| 5,913,876 A | 6/1999 | Taylor et al. |
| 5,927,284 A | 7/1999 | Borst et al. |
| 5,931,778 A | 8/1999 | Furnish |
| 5,944,658 A | 8/1999 | Koros et al. |
| 5,944,736 A | 8/1999 | Taylor et al. |
| 5,947,125 A | 9/1999 | Benetti |
| 5,947,896 A | 9/1999 | Sherts et al. |
| 5,957,835 A | 9/1999 | Anderson et al. |
| 5,967,972 A | 10/1999 | Santilli et al. |
| 5,967,973 A | 10/1999 | Sherts et al. |
| 5,967,974 A | 10/1999 | Nicholas et al. |
| 5,976,080 A | 11/1999 | Farascioni |
| 5,976,171 A | 11/1999 | Taylor |
| 5,984,865 A | 11/1999 | Farley et al. |
| 5,984,867 A | 11/1999 | Deckman et al. |
| 5,987,490 A | 11/1999 | Alidina et al. |
| 6,007,486 A | 12/1999 | Hunt et al. |
| 6,007,523 A | 12/1999 | Mangosong |
| 6,013,027 A | 1/2000 | Khan et al. |
| 6,015,378 A | 1/2000 | Borst et al. |
| 6,017,304 A | 1/2000 | Vierra et al. |
| 6,019,722 A | 2/2000 | Spence et al. |
| 6,024,720 A | 2/2000 | Chandler et al. |
| 6,030,340 A | 2/2000 | Maffei et al. |
| D421,803 S | 3/2000 | Koros et al. |
| 6,032,672 A | 3/2000 | Taylor |
| 6,033,362 A | 3/2000 | Cohn |
| 6,036,641 A | 3/2000 | Taylor et al. |
| 6,050,266 A | 4/2000 | Benetti et al. |
| 6,056,689 A | 5/2000 | Lenox et al. |
| 6,063,021 A | 5/2000 | Hossain et al. |
| 6,071,295 A | 6/2000 | Takahashi |
| 6,074,343 A | 6/2000 | Nathanson et al. |
| 6,096,046 A | 8/2000 | Weiss |
| 6,099,468 A | 8/2000 | Santilli et al. |
| 6,102,853 A | 8/2000 | Scirica et al. |
| 6,102,854 A | 8/2000 | Cartier et al. |
| 6,120,436 A | 9/2000 | Anderson et al. |
| 6,132,370 A | 10/2000 | Furnish et al. |
| 6,139,492 A | 10/2000 | Vierra et al. |
| 6,149,583 A | 11/2000 | Vierra et al. |
| 6,152,874 A | 11/2000 | Looney et al. |
| 6,162,172 A | 12/2000 | Cosgrove et al. |
| 6,183,486 B1 | 2/2001 | Snow et al. |
| 6,190,311 B1 | 2/2001 | Glines et al. |
| 6,193,651 B1 | 2/2001 | DeFonzo |
| 6,193,652 B1 | 2/2001 | Berky et al. |
| 6,200,263 B1 | 3/2001 | Person |
| 6,206,826 B1 | 3/2001 | Mathews et al. |
| 6,206,827 B1 | 3/2001 | Chin et al. |
| 6,206,828 B1 | 3/2001 | Wright |
| 6,210,323 B1 | 4/2001 | Gilhuly et al. |
| 6,213,940 B1 | 4/2001 | Sherts et al. |
| 6,213,941 B1 | 4/2001 | Benetti et al. |
| 6,224,545 B1 | 5/2001 | Cocchia et al. |
| 6,231,506 B1 | 5/2001 | Hu et al. |
| 6,254,532 B1 | 7/2001 | Paolitto et al. |
| 6,258,023 B1 | 7/2001 | Rogers et al. |
| 6,264,605 B1 | 7/2001 | Scirica et al. |
| 6,273,853 B1 | 8/2001 | Cartier et al. |
| 6,283,912 B1 | 9/2001 | Hu et al. |
| 6,290,644 B1 | 9/2001 | Green, II et al. |
| 6,306,085 B1 | 10/2001 | Farascioni |
| 6,309,349 B1 | 10/2001 | Bertolero et al. |
| 6,315,717 B1 | 11/2001 | Benetti et al. |
| 6,322,500 B1 * | 11/2001 | Sikora et al. ............... 600/219 |
| 6,331,158 B1 | 12/2001 | Hu et al. |
| 6,346,077 B1 | 2/2002 | Taylor et al. |
| 6,348,036 B1 | 2/2002 | Looney et al. |
| 6,371,911 B1 | 4/2002 | Hossain et al. |
| 6,394,951 B1 | 5/2002 | Taylor et al. |
| 6,416,468 B2 | 7/2002 | Deckman et al. |
| 6,416,469 B1 | 7/2002 | Phung et al. |
| 6,416,470 B2 | 7/2002 | Paolitto et al. |
| 6,458,079 B1 | 10/2002 | Cohn et al. |
| 6,478,729 B1 | 11/2002 | Rogers et al. |
| 6,500,116 B1 | 12/2002 | Knapp |
| 6,511,416 B1 | 1/2003 | Green, II et al. |
| 6,530,883 B2 | 3/2003 | Bookwalter et al. |

| | | |
|---|---|---|
| 6,537,212 B2 | 3/2003 | Sherts et al. |

FOREIGN PATENT DOCUMENTS

| | | |
|---|---|---|
| CA | 451133 | 9/1948 |
| CA | 2216893 | 2/1999 |
| EP | 246086 | 11/1987 |
| EP | 293760 | 12/1988 |
| EP | 336526 | 10/1989 |
| EP | 0 630 629 A1 | 12/1994 |
| EP | 0 791 330 A2 | 8/1997 |
| EP | 803228 | 10/1997 |
| EP | 0 820 821 A1 | 1/1998 |
| EP | 0 920 835 A1 | 6/1999 |
| EP | 993806 | 4/2000 |
| FR | 1005345 | 4/1952 |
| GB | 2102681 | 2/1983 |
| GB | 2233561 | 1/1991 |
| GB | 2 267 827 A | 12/1993 |
| WO | 8904145 | 5/1989 |
| WO | 9221296 | 10/1992 |
| WO | WO 94/14383 | 7/1994 |
| WO | 9418881 | 9/1994 |
| WO | 9421179 | 9/1994 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | 9726828 | 7/1997 |
| WO | 9732514 | 9/1997 |
| WO | 9740738 | 11/1997 |
| WO | 9740752 | 11/1997 |
| WO | WO 98/17182 | 4/1998 |
| WO | WO 98/27869 | 7/1998 |
| WO | 9848703 | 11/1998 |
| WO | 9849944 | 11/1998 |
| WO | 9849947 | 11/1998 |
| WO | 9908585 | 2/1999 |
| WO | 9909892 | 3/1999 |
| WO | 9916367 | 4/1999 |
| WO | 0006041 | 2/2000 |
| WO | 0042920 | 7/2000 |
| WO | 0042921 | 7/2000 |
| WO | 0042935 | 7/2000 |
| WO | 0042936 | 7/2000 |
| WO | 0042937 | 7/2000 |
| WO | 0103585 | 1/2001 |

OTHER PUBLICATIONS

"Direct Myocardial Revascularization without Extracorporeal Circulation", Benetti MD, et al., Chest/100/2/Aug. 1991, pp. 313–316.

"Current Status of Cardiac Surgery: A 40 Year Review", Richenbacher MD, et al., Journal of the American College of Cardiology, 1989, pp. 535–544.

"Delayed Recovery of Severely "Stunned" Myocardium With the Support of a Left Ventricular Assist Device After Coronary Artery bypass Graft Surgery", Ballantyne MD, et al., Journal of the American College of Cardiology, 1987, pp. 1–3.

"Enhanced preservation of Acutely Ischemic Myocardium With Transseptal Left Ventricular Assist", Fonger MD, et al., The Annals of Thoracic Surgery, vol. 57, No. 3, Mar. 1994, pp. 1–6.

Barbut et al., "Cerebral Emboli Detected During Bypass Surgery Are Associated With Clamp Removal," Stroke, 25(12):2398–2402 (1994).

Barbut et al., "Comparison of Transcranial Doppler Ultrasonography and Transesophageal Echocardiography to Monitor Emboli During Coronary Artery Bypass Surgery," Stroke 27(1):87–90 (1996).

Barbut et al., "Aortic Atheromatosis and Risks of Cerebral Embolization," Journal of Cardiothoracic and Vascular Anesthesia 10(1):24–30 (1996).

van der Linden et al., "When Do Cerebral Emboli Appear During Open Heart Operations? A Transcrainial Doppler Study," Ann. Thorac. Surg. 51:237–241 (1991).

M. Vigano, "Applicazione dell'archetto di divaricamento vasale in corso di chirurgia coronarica," Minerva Cardioangiologica, 23, 369–371, 1975.

S. Westaby et al., "Less Invasive Coronary Surgery: Consensus From the Oxford Meeting," Ann Thorac Surg 1996;62:924–31.

J. G. Vincent, "A compact single post internal mammary artery dissection retractor," European Journal of Cardio–thoracic Surgery, (1989) 3:276–277.

Brochure, USSC Cardiovascular "Thora–LIFT".

J. Stevens et al., "Closed–Chest Coronary Artery Bypass with Cardioplegic Arrest in the Dog," Circulation, vol. 90, No. 4, Part 2, Oct. 1994, Abstracts from the 67th Scientific Sessions, Dallas, TX, Nov. 14–17, 1994.

D. Roux et al., "Internal mammary artery dissection: A three dimensional sternal retractor," J. Cardiovasc. Surg., 30, p 996, 1989.

D. Roux et al., "New Helper Instrument in Cardiac Surgery," Ann Thorac Surg 1989;48:595–96.

J. Rousou et al., "Cardiac Retractor for Coronary Bypass Operations," Ann Thorac Surg 1991;52:877–8.

F. Robicsek, "Aortic Spoon–Jaw Clamp for Aorto–Saphenous Vein Anastomosis," J Card Surg 1995;10:583–585.

J. Pittman et al., "Improved Visualization of the Internal Mammary Artery With a New Retractor System," Ann Thorac Surg 1989;48:869–70.

Brochure, Pilling Surgical Instruments, "Wishbone Retractor System" and "Retractors—Self Retaining".

S. Phillips et al., "A versatile retractor for use in harvesting the internal mammary artery and performing standard cardiac operations," J Thorac Cardiovasc Surg 1989;97:633–5.

L. Perrault et al., "Snaring of the Target Vessel in Less Invsive Bypass Operations Does Not Cause Endothelial Dysfunction," Ann Thorac Surg 1997;63:751–5.

V. Parsonnet et al., "Self–retaining epicardial retractor for aortocoronary bypass surgery," The Journal of Thoracic and Cardiovascular Surgery, p 629–630, 1979.

V. Parsonnet et al., "Graduated probes for coronary bypass surgery," The Journal of Thoracic and Cardiovascular Surgery, vol. 68, No. 3, p. 424, Sep. 1974.

J. Ochsner et al., "Surgical Management of Diseased Intracavitary Coronary Arteries," The Annals of Thoracic Surgery, vol. 38, No. 4, p. 356, Oct. 1984.

S. Eguchi, "A Special Retractor for Stabilizing the Heart During Circumflex Coronary Grafting".

S. Kazama et al., "Fabric Heart Retractor for Coronary Artery Bypass Operations," Ann Thorac Surg 1993;55:1582–3.

P. McKeown et al., "A Modified Sternal Retractor for Exposure of the Internal Mammary Artery," Ann Thorac Surg, 1980.

A. Matsuura et al., "A New Device for Exposing the Circumflex Coronary Artery," Ann Thorac Surg 1995;59:1249–50.

S. Murata et al., "Revascularization of the Circumflex Coronary Artery—A New Instrument and A Technical Method – ," The Japanese Journal of Thoracic Surgery, vol. 42, No. 2, 1989, p. 115.

T. Konishi et al., "Hybrid–Type Stabilizer for Off–Pump Direct Coronary Artery Bypass Grafting," The Annals of Thoracic Surgery, vol. 66, No. 3, Sep. 1998, p. 962.

T. Itoh et al., "New Modification of a Mammary Artery Retractor," Ann Thorac Surg 1994;57:1670–1.

G. Green, "Technique of internal mammary–coronary artery anastomosis," J Thorac Cardiovasc Surg 78:455–459, 1979.

J. Groopman, "Heart Surgery, Unplugged," The New Yorker, Jan. 11, 1999, p. 43.

F. Guzman et al., "Transient radial nerve injury related to the use of a self retaining retractor for internal mammary artery dissection," J Cardiovasc Surg, 30, 1989, p. 1015.

R. Hasan et al., "Technique of dissecting the internal mammary after using the moussalli bar," Eur J Cardio–thorac Surg (1990) 4:571–572.

I. Donald et al., "'Snake' Flexible Arm," British Medical Journal, Oct. 19, 1968, p. 170.

A. DelRossi et al., "A New Retractor to Aid in Coronary Artery Surgery," The Annals of Thoracic Surgery, vol. 36, No. 1, Jul. 1983, p. 101.

Brochure, "DeLacroix–Chevalier Surgical Instruments, IMA Savings Packages".

B. Cutler et al., "New Use for an Old Clamp," Arch Surg, vol. 115, Sep. 1980, p. 1136.

J. Cremer et al., "Off–Bypass Coronary Bypass Grafting via Minithoracotomy Using Mechanical Epicardial Stabilization," Ann Thorac Surg 1997;63:S79–83.

C. Antinori et al., "A Method of Retraction During Reoperative Coronary Operations Using the Favaloro Retractor," Ann Thorac Surg 1989;48:440.

G. Angelini et al., "A Fiber–Optic Retractor for Harvesting the Internal Mammary Artery," Ann Thorac Surg 1990;50:314–5.

A. Cohen et al., "Mini–Sternotomy for Coronary Artery Bypass Grafting," Ann Thorac Surg 1996;62:1883–92.

R. Beg et al., "Internal Mammary Retractor," The Annals of Thoracic Surgery, vol. 39, No. 1, Jan. 1985.

S. Westaby, "Coronary surgery without cardiopulmonary bypass," Br Heart J 1995;73:203–205.

A. Calafiore et al., "Minimally Invasive Coronary Artery Bypass Grafting," Ann Thorac Surg 1996;62:1545–8.

R. Cartier et al., "Triple Coronary Artery Revascularization on the Stabilized Beating Heart: Initial Experience," CJS, vol. 41, No. 4, Aug. 1998.

N. Ancalmo et al., "A Modified Sternal Retractor," The Annals of Thoracic Surgery, vol. 21, Jan.–Jun. 1976.

D. Cooley, "Limited Access Myocardial Revascularization, A Preliminary Report," Texas Heart Institute Journal, vol. 23, No. 2, 1996.

G. Angelini, "A Simple, Inexpensive Method of Heart Retraction During Coronary Artery Bypass Surgery," Ann Thorac Surg 46:246–247, Aug. 1988.

K. Arom et al., "Mini–Sternotomy for Coronary Artery Bypass Grafting," Ann Thorac Surg 1996;61:1271–2.

M. Bedellino et al., "The Cardiac Rag, Simple Exposure of the Heart," Texas Heart Institute Journal, vol. 15, No. 2, 1988.

J. Bonatti et al., "Single coronary artery bypass grafting—a comparison between minimally invasive 'off pump' techniques and conventional procedures," European Journal of Cardio–thoracic Surgery 14 (Suppl. 1) (1998) S7–S12.

M. Bugge, "A New Internal Mammary Artery Retractor," Thorac. Cardiovasc. Surgeon 38 (1990) 316–317.

G. Campalani et al., "A new self–retaining internal mammary artery retractor," J Cardiovasc Surg. 28, 1987.

A. Chaux, et al., "A New Concept in Sternal Retraction: Applications for Internal Mammary Artery Dissection and Valve Replacement Surgery," Ann Thorac Surg 42:473–474, Oct. 1986.

Brochure, Chase Medical, "Beating Heart Technology, Heart to Heart Innovation".

G. D. Buckberg, "Strategies and Logic of Cardioplegic Delivery to Prevent, Avoid, and Reverse Ischemic and Reperfusion Damage," 93 The Journal of Thoracic and Cardiovascular Surgery, p. 127–139 (Jan. 1987).

G. D. Buckberg, "Retrograde Pulmonary Venous Pressure Measurement—Fact or Artifact?", The Journal of Thoracic and Cardiovascular Surgery, vol. 59, No. 3, pp. 393–406, Mar. 1970.

H. V. Liddle et al., "Metabolic Management of the Myocardium During Cardiac Surgery", Blades Surgical Diseases of the Chest, Chapter 23, pp. 649–671.

P. Menasche et al., "Retrograde Coronary Sinus Perfusion: A Safe Alternative for Ensuring Cardioplegic Delivery in Aortic Valve Surgery", The Annals of Thoracic Surgery, vol. 34, No. 6, Dec. 1982, pp. 647–658.

J. Solorzano et al., "Retrograde Coronary Sinus Perfusion for Myocardial Protecting During Cardiopulmonary Bypass", The Annals of Thoracic Surgery, vol. 25, No. 3, Mar. 1978, pp. 201–208.

G. Pennington, "Direct Coronary Ostial Perfusion", Myocardial Protection in Cardiac Surgery, edited by Arthur J. Roberts, published by Marcel Dekker Corp., New York and Basel, 1067, pp. 229–250.

International Working Group on Coronary Sinus Interventions, Newsletter, vol. 1, No. 3, Oct., 1987.

Partington, article covering the background for the use of antegrade/retrograde cardioplegic in combination submitted to The Journal of Thoracic and Cardiovascular Surgery.

R. Poirier et al., "Drip Retrograde Coronary Sinus Perfusion for Myocardial Protection During Aortic Cross–Clamping," The Journal of Thoracic and Cardiovascular Surgery, vol. 70, No. 6, Dec. 1975, p. 966.

G. Smith et al., "Reduction in Infarct Size by Synchronized Selective Coronary Venous Retroperfusion of Arterialized Blood," The American Journal of Cardiology, vol. 48, p. 1064 (Dec. 1981).

S. Gundry, "Modification of Myocardial Ischemia in Normal and Hypertrophiced Hearts Utilizing Diastolic Retroperfusion of the Coronary Veins," J. Thoracic & Cardiovascular Surgery, pp. 659–669 (May 1982).

S. Meerbaum et al., "Hypothermic Coronary Venous Phased Retroperfusion: A Closed–chest Treatment of Acute Regional Myocardial Ischemia," Circulation vol. 65, No. 7, p. 1435 (Jun. 1982).

H. DeYoung, "State of the Heart," High Technology May 1984, p. 33.

V. Gott et al., "Retrograde Perfusion of the Coronary Sinus for Direct Vision Aortic Surgery," (Surgery, Gynecology & Obstetrics, Mar. 1957), p. 319.

S. Meerbaum et al., "Diastolic Retroperfusion of Acutely Ischemic Myocardium" (The American Journal of Cardiology, vol. 37, Mar. 1976), p. 588.

A. Berdeaux et al., "Effects of Diastolic Synchronized Retroperfusion on Regional Blood Flow in Experimental Myocardial Ischemia," (The American Journal of Cardiology, vol. 47, May 1981).

J. Farcot et al., "Synchronized Retroperfusion of Coronary Veins for Circulatory Support of Jeopardized Ischemic Myocardium," (The American Journal of Caradiology, vol. 41, Jun. 1978).

M. Feola et al., "A Method of Coronary Retroperfusion for the Treatment of Acute Myocardial Ischemia," (Cardiovascular Diseases, Bulletin of The Texas Heart Institute, vol. 5, No. 3, Sep. 1978).

CTS® AuroraTM MultiTrac System Product Brochure, CardioThoracic Systems Inc., Cupertino, CA.

OPCABTM Access Systems Product Brochure, CardioThoracic Systems Inc., Cupertino, CA.

CTS® Access UltimaTM System Product Brochure, CardioThoracic Systems Inc., Cupertino, CA.

M. Bashar Izzat et al., "Cardiac Stabilizer for Minimally Invasive Direct Coronary Artery Bypass," Ann Thorac Surg 1997; 64:570–1.

M. Riahi et al., "A simple technique and device to provide a bloodless operative field in coronary artery surgery without cross–clamping the aorta," The Journal of Thoracic and Cardiovascular Surgery, vol. 66, No. 6, pp. 974–978.

A. Elami et al., "Technique for Reoperative Median Sternotomy in the Presence of a Patent Left Internal Mammary Artery Graft," J Card Surg 1994; 9:123–127.

M. Fackler, "Extending the Usefulness of Self–Retaining Retraction," The American Journal of Surgery, vol. 129, Jun. 1975, pp. 712–715.

I. Galvin et al., "Circumflex Exposure Using a Cardiac Sling," Ann Thorac Surg 1990; 49:833–4.

P. Grundeman et al., "Hemodynamic Changes During Displacement of the Beating Heart by the Utrecht Octopus Method," Ann Thorac Surg 1997; 63:S88–92.

R. Hartz, "Minimally Invasive Heart Surgery," Circulation, 1996; 94:2669–2670.

A. Matsuura et al., "Modified Janke Net Technique for Exposure of the Circumflex Artery," Thorac. Cardiovasc. Surgeon 40 (1992) 158–159.

Y. Moshkovitz et al., "Coronary Artery Bypass Without Cardiopulmonary Bypass: Analysis of Short–term and Mid–term Outcome in 220 Patients," J Thorac Cardiovasc Surg 1995; 110:979–87.

V. Mueller, "Microsurgery: The New Frontier," 1968.

M. Robinson et al., "Minimally Invasive Coronary Artery Bypass Grafting: A New Method Using an Anterior Mediastinotomy," J Card Surg 1995; 10:529–536.

G. Sani et al., "Coronary surgery without cardiopulmonary bypass," Cardiologia 1995; 40 (11): 857–863.

M. Sweeney et al., "Device–Supported Myocardial Revascularization: Safe Help for Sick Hearts," Ann Thorac Surg 1992; 54:1065–70.

A. Eguchi, "Heart Retractor for Use in Anastomosis in Coronary Artery By–Pass Surgery," Japanese Journal of Thoracic Surgery, vol. 40 No. 1, 1987.

L. Bonchek, "Technical Considerations for Coronary Artery Bypass Without Cardioplegia," Journal of Cardiac Surgery, vol. 7, No. 4, 1992, pp. 333–341.

C. Borst et al., "Regional Cardiac Wall Immobilization for Open Chest and Closed Chest Coronary Artery Bypass Grafting on the Beating Heat: The 'Octopus' Method," Circulation, vol. 92, Suppl. 1 pp. 1–176—1–177 (Oct. 15, 1995); Cardio–Thoracic and Vascular Surgery: Abstracts 0840–0851.

Miltex Surgical Instruments Catalog, pp. 298–299.

V. Mueller, JANNETTA Retractor Set, LEYLA Self–Retaining Brain Retractor, neurological Instruments, pp. 17–18.

Pilling Surgical Instruments Catalog, p. 304, 1993.

Aesculap Catalog, Separadores costales, p. 630.

Chase Medical Brochure, "EPRetractTM ClearAssistTM", 2001.

Y. Bar–El et al., "Clamping of the atherosclerotic ascending aorta during coronary artery bypass operations, Its cost in stokes," J Thorac Cardiovasc Surg 1992; 104:469–474.

"Heart–mechanical Assist Device Interaction", Kresh, et al., vol. XXXII ASAIO 1987, pp. 437–443.

"Long–term Follow–up of Survivors of Postcardiotomy Circulatory Support", Ruzevich, et al., vol. XXXIV ASAIO 1988, pp. 116–124.

"Extended Clinical Support with an Implantable Left Ventricular Assist Device", McGee, et al. vol. XXXV ASAIO 1989, pp. 614–616.

"Coronary Artery Bypass Without Cardiopulmonary Bypass", Pfister, MD, et al.,The Society of Thoracic Surgeons, Feb. 3–5, 1992, pp. 1085–1092.

"Reoperative Coronary Artery Bypass Grafting Without Cardiopulmonary Bypass", Fanning MD, et al.,The Society of Thoracic Surgeons 1993, pp. 486–489.

"Placement of Coronary Artery Bypass Graft Without Pump Oxygenator", Trapp MD, et al.,The Annals of Thoracic Surgery, vol. 19, No. 1, 1975, pp. 1–9.

Direct Mechanical Ventricular Actuation for Cardiac Arrest in Humans', Anstadt MD, et al.,57th Annual Scientific Assembly, San Francisco, Nov. 4–8–1991, pp. 86–92.

"Transfemoral Placement of the Left Ventricular Assist Device "Hemopump" During Mechanical Resuscitation", Scholz, et al., Thoracic and Cardiovascular Surgeon, vol. 28, Feb. 1990, pp. 69–72.

"Cardiogenic Shock Complicating Acute myocardial Infraction: The Use of Coronary Angioplasty and the Integration of the New Support Devices into patient Management", Gacioch MD, Journal of the American College of Cardiology, vol. 19, pp. 647–653.

"Mammary artery–coronary artery anastomosis as method of treatment for angina pectoris", Kolessov MD, Journal of Thoracic and Cardiovascular Surgery, vol. 54, No. 4, Oct. 1967, pp. 535–544.

"Direct coronary surgery with saphenous vein bypass without either cardiopulmonary bypass or cardiac arrest", Benetti, Official Journal of the International Society for Cardiovascular Surgery, vol. 26, No. 3, May–Jun. 1985, pp. 217–222.

"A Prospective Evaluation of the Pulsatile Assist Device", Zumbro, Jr. MD et al., The Annals of Thoracic Surgery, No. 2, Aug. 1979, pp. 269–273.

"Direct Myocardial Revascularization by Saphenous Vein Graft", Favaloro MD, et al., The Annals of Thoracic Surgery, vol. 10, No. 2, Aug. 1970, pp. 97–111.

"Preservation of interventricular septal function in patients having coronary artery bypass grafts without cardiopulmonary bypass", Akins MD, et al., American Heart Journal, vol. 107, No. 2, pp. 304–309.

"Direct Myocardial Revascularization without Cardiopulmonary Bypass", Buffolo et al., Thoracic Cardiovascular Surgeon, 1985, pp. 1–4.

"Coronary Artery Operation with Support of the Hemopump Cardiac Assist System", Lonn MD, et al., The Society of Thoracic Surgeons, 1994, pp. 1–5.

"Coronary Artery Operation Supported by the Hemopump: An Experimental Study on Pig", Lonn MD, et al., The Society of Thoracic Surgeons, 1994, pp. 516–518.

"Coronary Artery Revascularization without Cardiopulmonary Bypass", Archer DO, et al., Texas Heart Institute Journal, vol. 11, No. 1, Mar. 1984, pp. 52–57.

Coronary Artery Bypass Grafting Without Cardiopulmonary Bypass and Without Interruption of Native Coronary Flow using a Novel Anastomosis Site Restraining Device ("Octopus"), Borst MD, et al., American College of Cardiology, vol. 27, 1996, pp. 1356–1364.

"Weck Surgical Instruments and Products", Pilling Weck, Research Triangle Park, NC, pp. 19–25.

"Coronary Artery Disease–Physiologic Concepts–Surgical Operation", Beck MD, Annals of Surgery, Apr. 1957, vol. 145, No. 4, pp. 439–460.

* cited by examiner

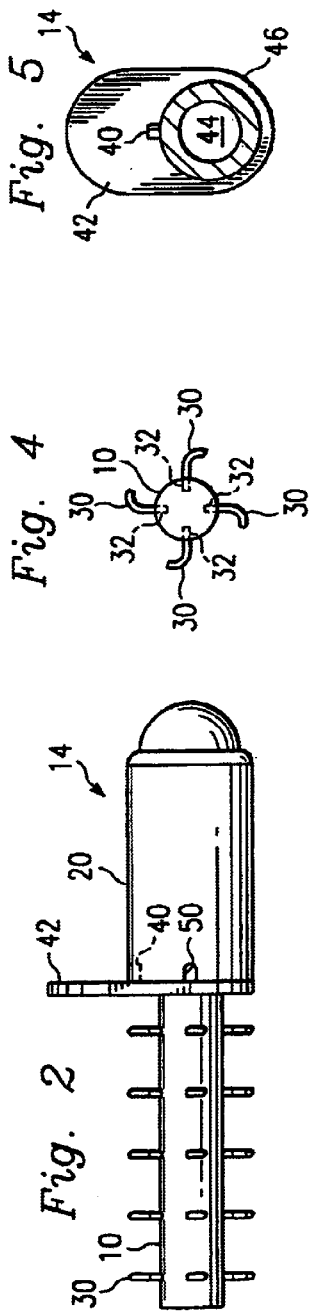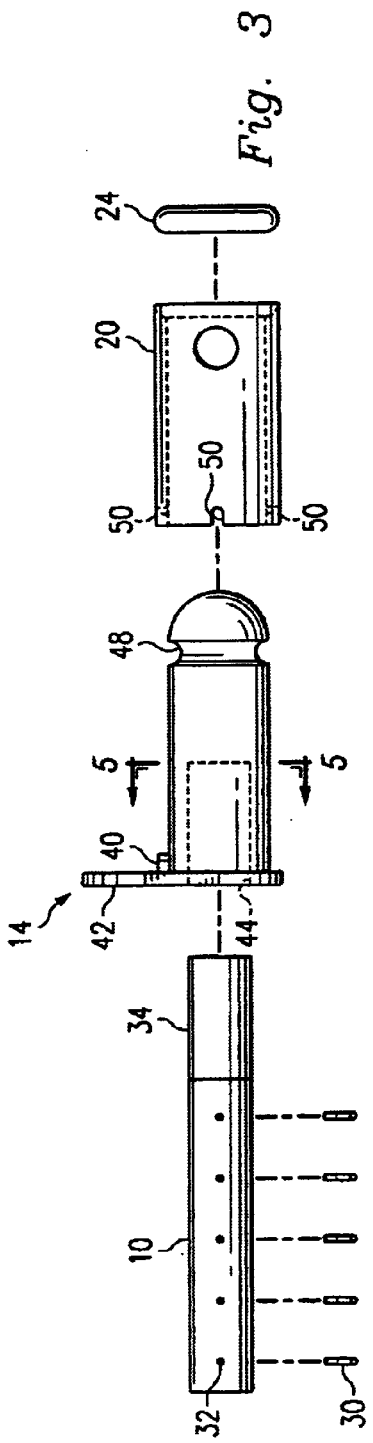

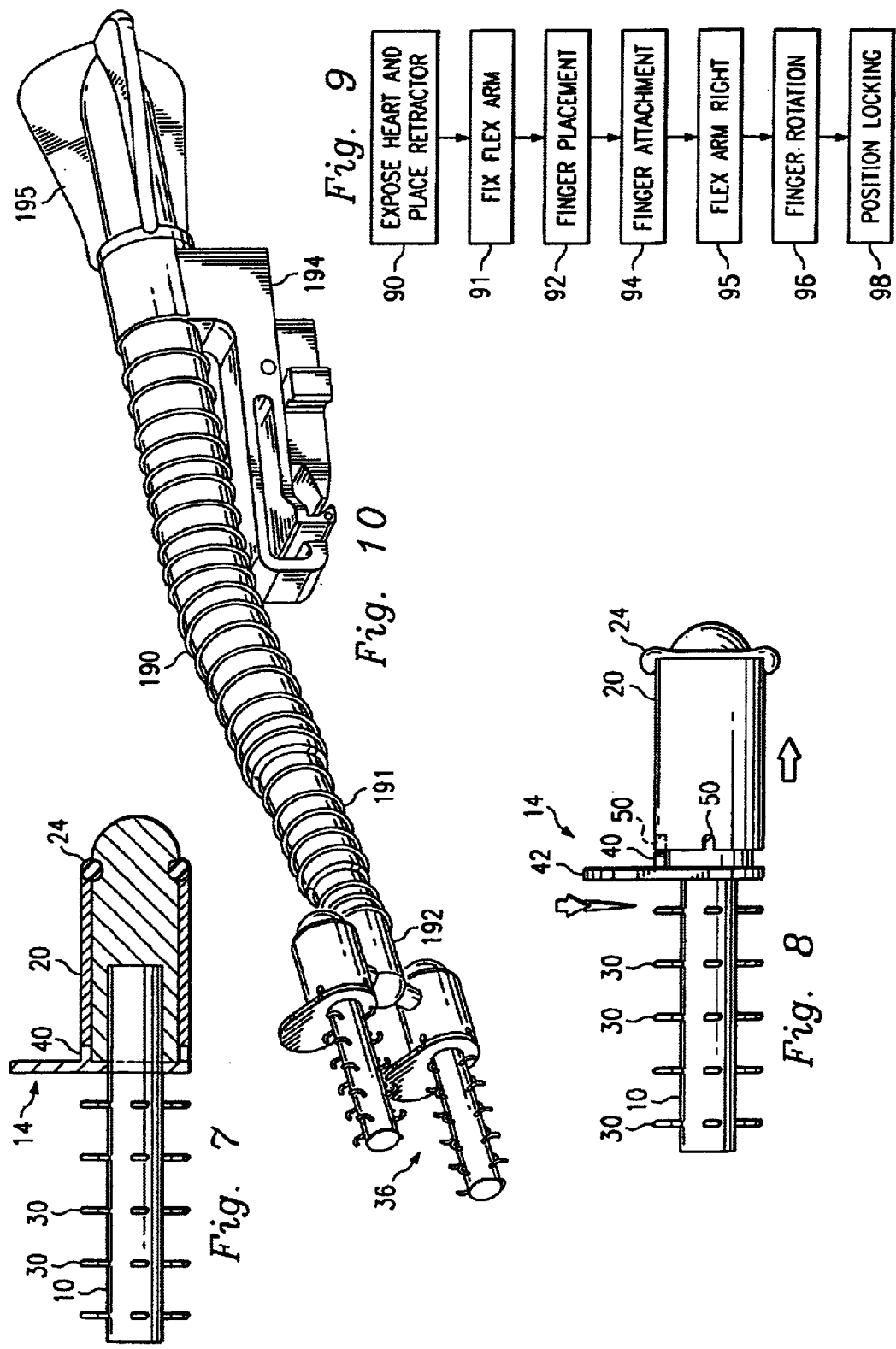

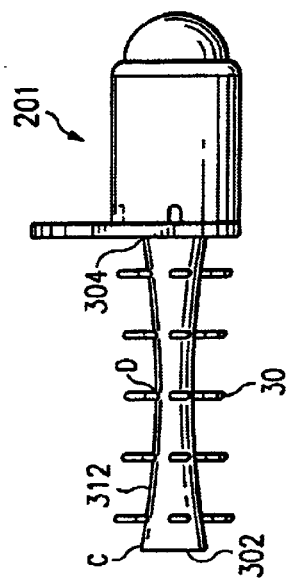
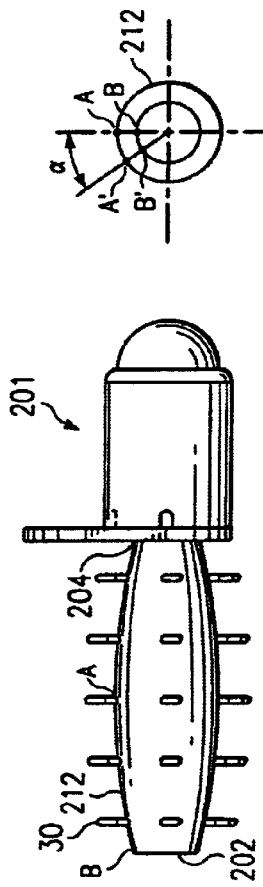
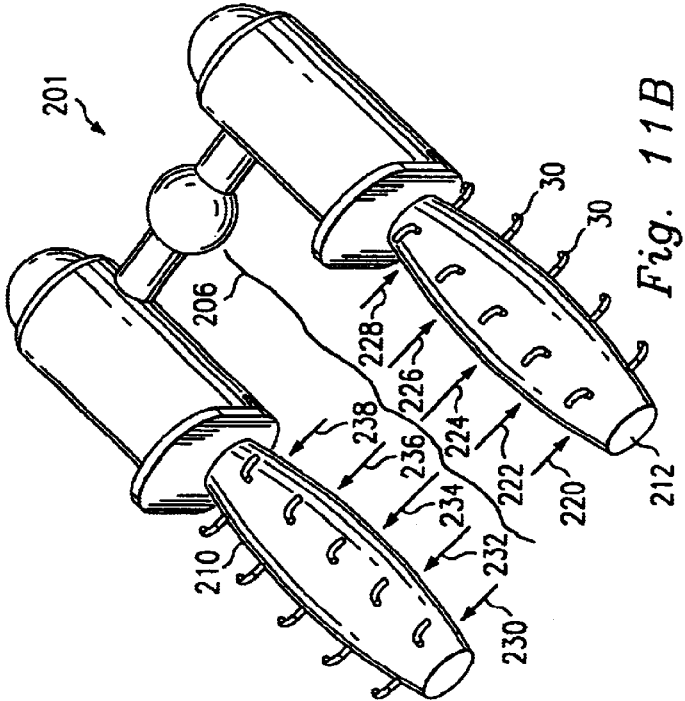
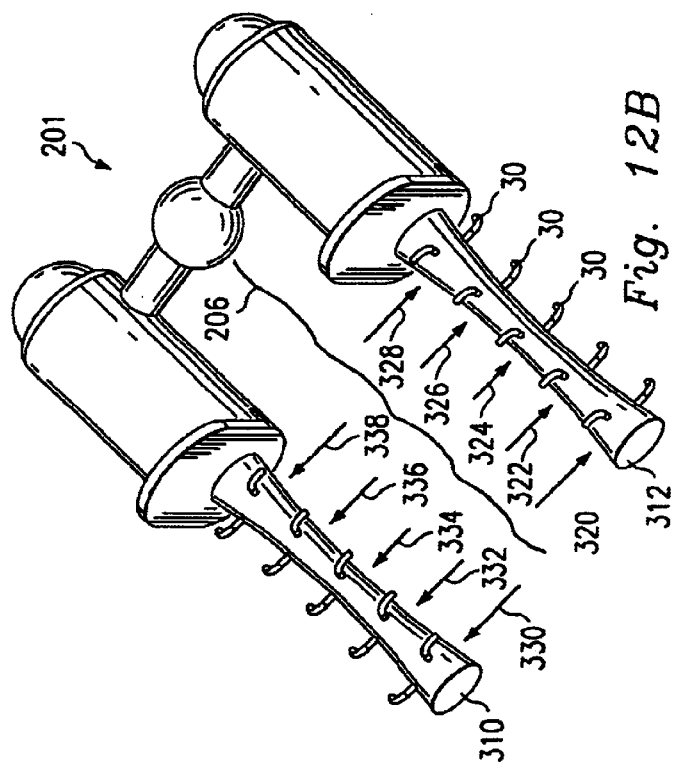

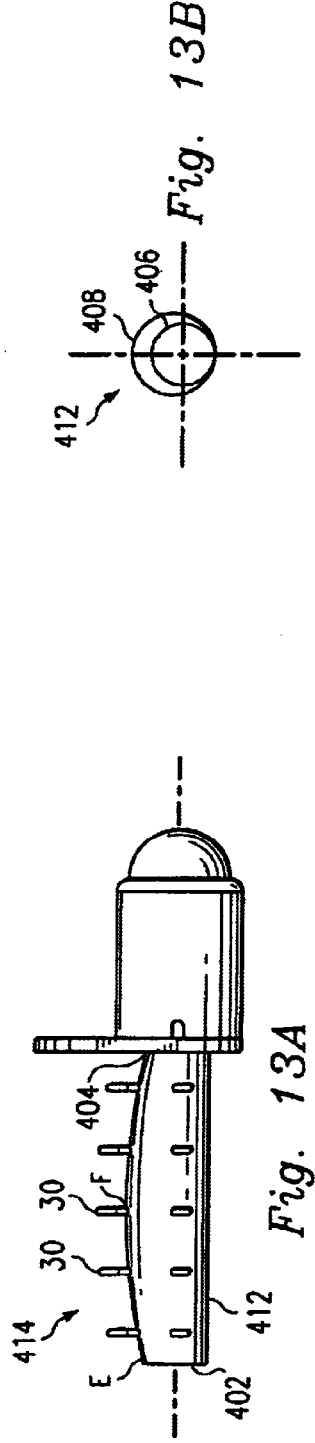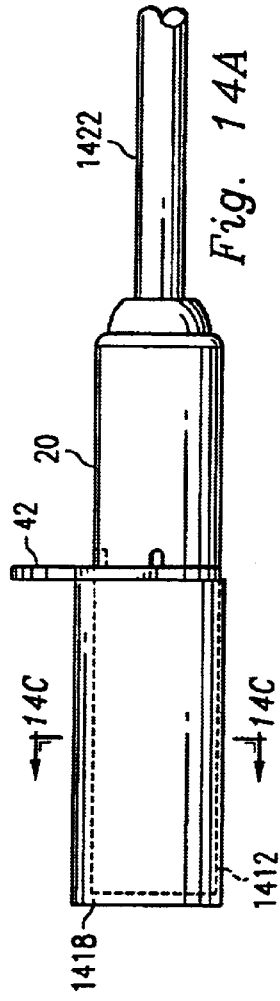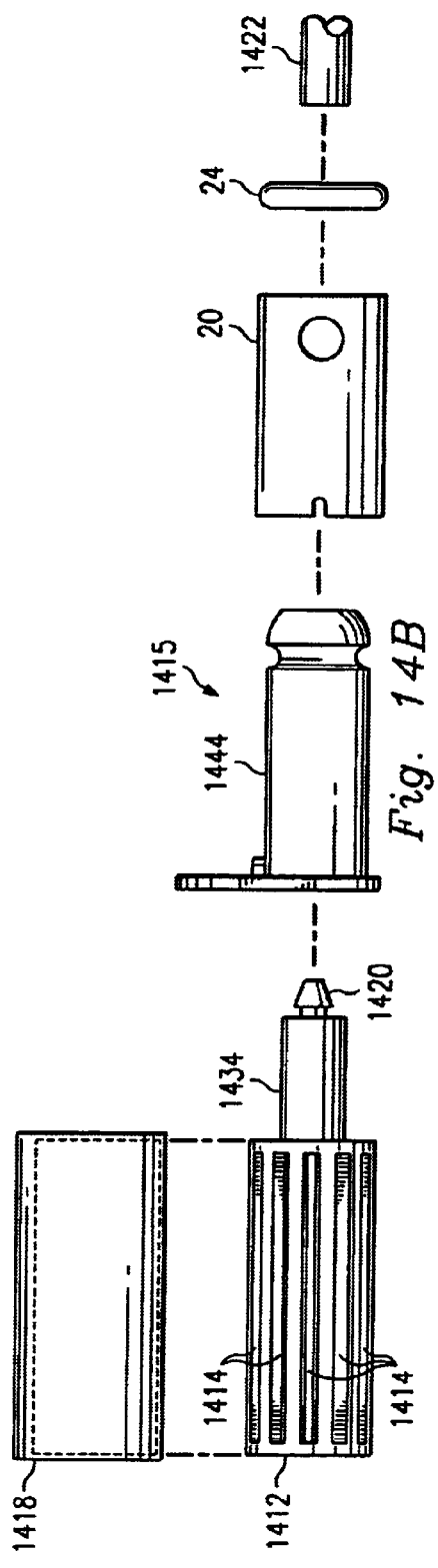

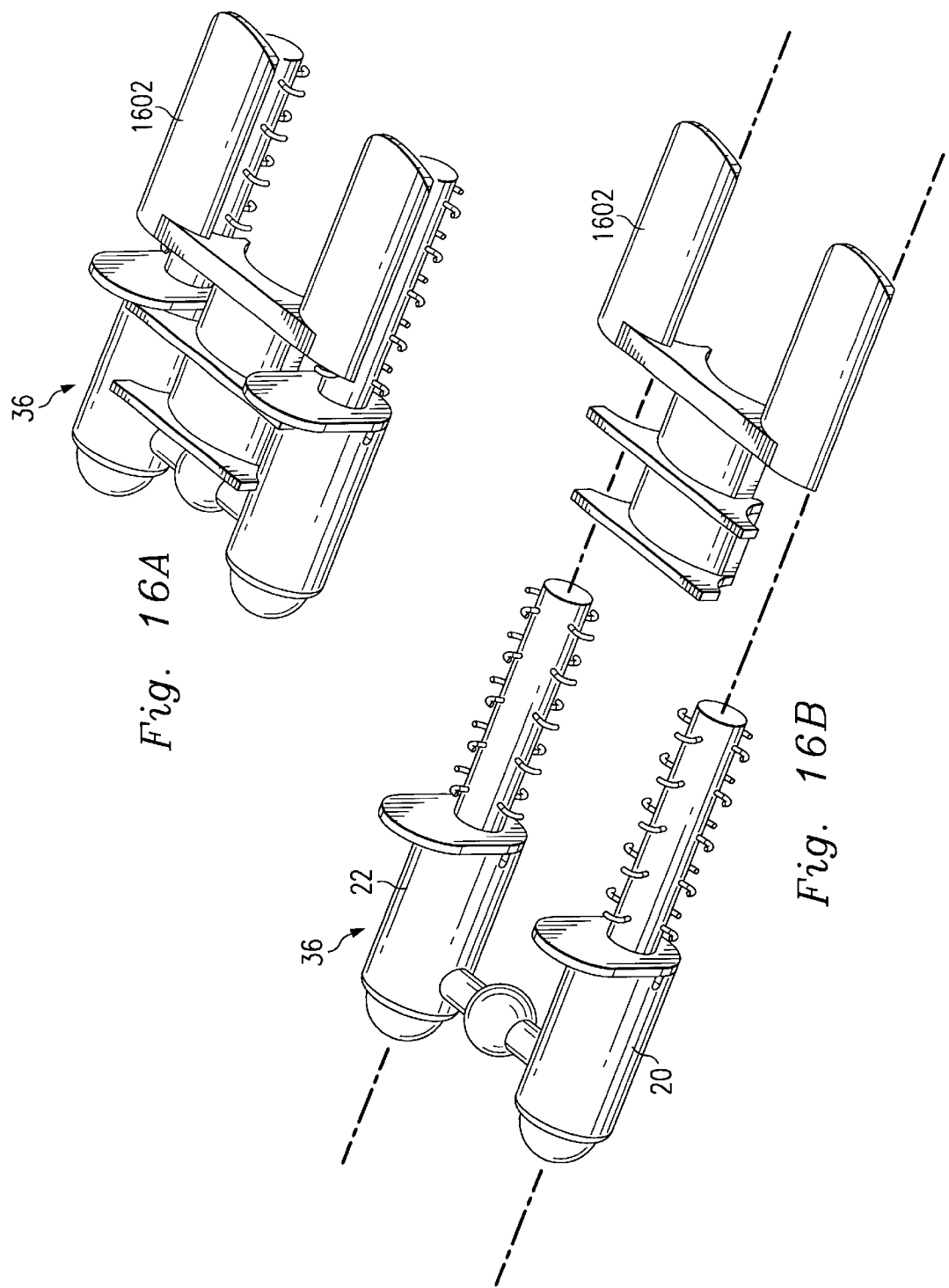

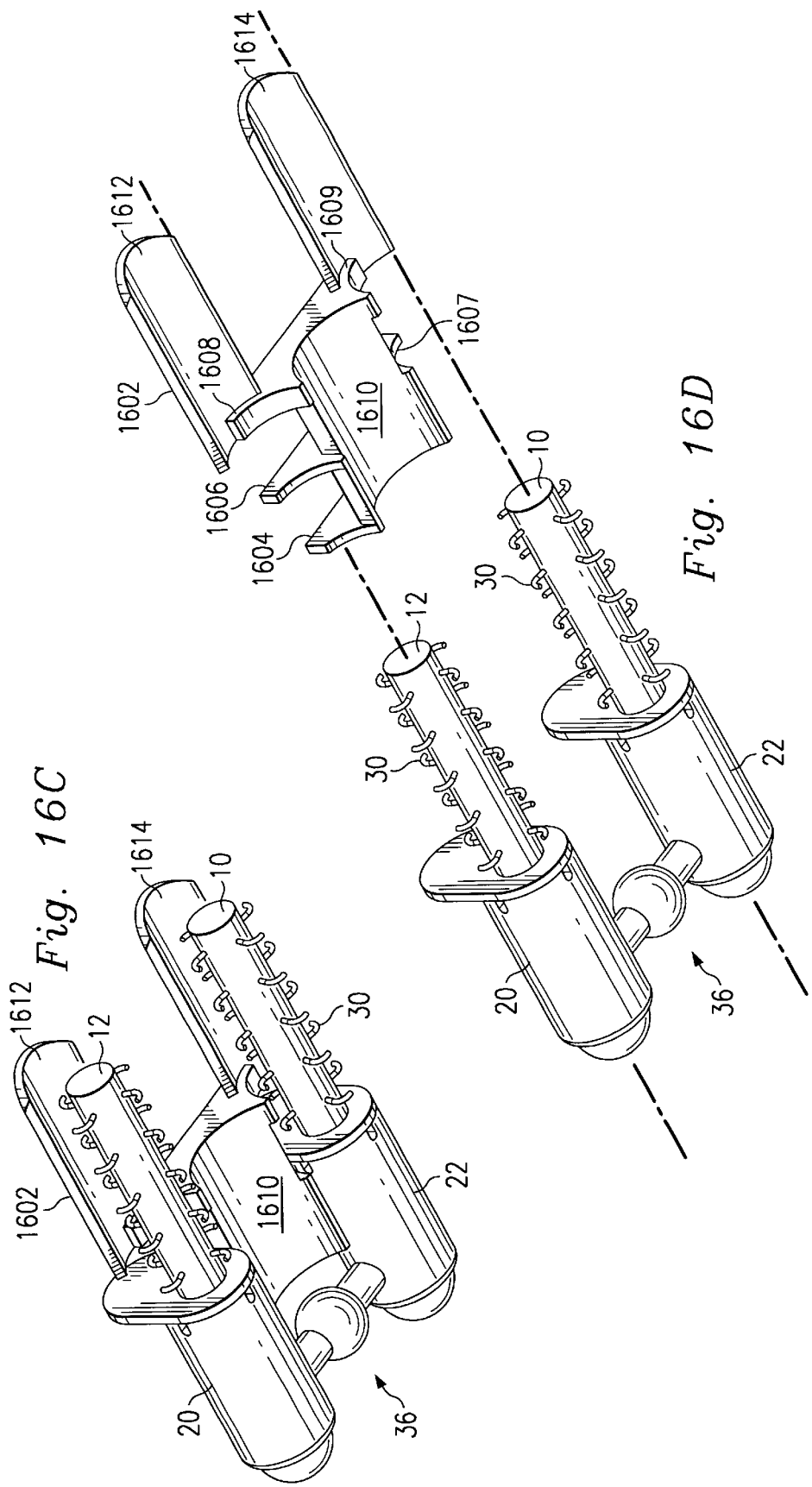

DEVICE AND METHOD FOR ISOLATING A SURFACE OF A BEATING HEART DURING SURGERY

CROSS REFERENCE

This application is a continuation of U.S. Ser. No. 09/632,430 filed on Aug. 4, 2000 which is a continuation in part of U.S. Ser. No. 09/376,538 filed Aug. 18, 1999, U.S. Pat. No. 6,258,023 which claims the benefit of U.S. Provisional application Serial No. 60/143,023, filed Jul. 8, 1999, the disclosures of which are hereby incorporated by reference.

FIELD OF THE INVENTION

The invention relates generally to medical surgical devices, and more particularly to a device and method of stabilizing a surgical site during cardiac or cardiovascular surgery.

BACKGROUND OF THE INVENTION

Heart disease and associated cardiovascular problems have become so common in the United States that over 400,000 open heart surgeries are performed each year. Traditionally, physicians would open the chest and stop the heart before performing a surgical procedure on the heart. However, medical practices have improved, and physicians now recognize that there are advantages to performing surgery on a beating heart. For example, performing surgery on a beating heart avoids the necessity to expose the heart to filters, oxygenators, tubes, and other devices. This decreases the trauma associated with stopping the heart, as well as avoids other dangers that stopping the heart poses to a patient. In addition, by avoiding the use of these devices, the physician can lower the expense of an operation. Furthermore, performing surgery on a beating heart lowers the risk of ischemic damage to heart and surrounding tissue.

Unfortunately, there are many difficulties and challenges which must be overcome to successfully perform surgery on a beating heart. For example, every time the heart beats, the heart moves. This makes it difficult to isolate a specific site on the heart for surgery. Furthermore, physicians typically must develop great skill and expertise to accommodate the movement of the heart with existing instruments which were designed for use with a heart that is stopped. Because of the increased demands of performing surgery on a beating heart, surgery on a beating heart often takes longer than surgery on a stopped heart. Fortunately, devices and methods are being developed which decrease the amount of time and expertise it takes to identify and isolate a target vessel and thus, reduce the time it takes to perform open heart surgery.

One family of instruments which have been developed to facilitate surgery on a beating heart are known as cardiac immobilization devices or heart stabilizers (devices). A number of these devices function by attaching to the heart at two or more points. The points are then moved further apart, thus stretching the surface area of the heart about which surgery is to be performed (surgical site). The devices typically grip the heart surface by suction. Unfortunately, there are a number of disadvantages associated with these methods of isolating a surgical site.

Some cardiac immobilization devices often appear to be little more than steak tongs or clamps which have been slightly altered to attach to a heart surface. Other devices use flex links or rods to attach to a retractor and then use a metallic foot to stabilize the heart surface. Suction devices may comprise a plurality of suction cups, or may have at least one hollow cylinder with holes in it, which is then attached to a pump which pulls a vacuum at the holes.

FIG. 1A (prior art) shows a cardiac immobilization device 130 attached to a heart surface 140. To perform open heart surgery, typically a chest retractor 110 is braced within a rib cage and used to maintain an opening in the chest wall 112 which provides access to the heart surface 140. A stabilizing member, such as a flexible arm assembly 120 is used to securely locate a cardiac immobilization device 130 upon the heart surface 140. Accordingly, the stabilizing member 120 is coupled to the retractor 110 via a clamp 126 and holds the cardiac immobilization device 130 in a predetermined position.

The flexible arm assembly 120 includes a flexible arm 124 which may be bent and twisted into various shapes and geometries to access different locations on the heart surface 140. At the end of the flexible arm 124 closest to the heart surface 140 is a socket 128 for attaching the flexible arm 124 to the cardiac immobilization device 130. At the other end of the flexible arm 124 is a handle 122 which when turned tightens a cable (not shown) within the flexible arm 124. The tightening of the cable makes the flexible arm 124 rigid and immobile. The tightening of the cable also tightens the socket 128, allowing the socket 128 to grip an object, such as a ball 132 (the ball 132 is part of the cardiac immobilization device 130).

The shown cardiac immobilization device 130 uses suction to attach to a surface of the heart 140. To attach the cardiac immobilization device 130 to the heart surface 140, the cardiac immobilization device 130 utilizes a foot plate 136 with holes thereunder (not shown) on which a vacuum is placed. The vacuum is maintained by air hoses 134 which are attached to an air pump (not shown) and the foot plate 136. Thus, the cardiac immobilization device 130 is held stationary on the heart surface 140 at the end of the flexible arm 124 of the flexible arm assembly 120 so that the heart surface 140 located within the foot plate 136 can be isolated.

One disadvantage of many tong type attachments is that they provide an uneven spread (the heart surface closest to the tong's hinge point is spread a smaller distance than the heart surface at the end of the tong).

There are also many disadvantages associated with using suction to isolate a surgical site. For example, many patients have a heart which is surrounded with fatty tissue. Since the fat surrounding the heart moves, when a physician uses a suction device to isolate a heart surface, the suction cups or suction holes attach to the fat (rather than the heart surface). The operative result of the device attaching to the fatty tissue is that the heart surface can still beat underneath the fatty tissue, which means that isolation and stabilization of the surgical site is poor. Furthermore, the fatty tissue may be drawn into the device (at a hole, for example) by the suction, and may clog the suction device thereby stopping suction at the holes which are further along and at the end of the device. In addition, after attachment to the heart is made with a suction device, the ability to spread the heart surface is limited by the force of suction on the heart surface. Should the suction break, the device must be repositioned and reattached to the heart, which consumes time and is a nuisance to the physician. Furthermore, when strong enough suction is applied to the heart surface to achieve adequate spreading and to prevent slippage, the suction can cause blood to accumulate and clot just beneath the heart surface, a hematoma (this condition is also commonly referred to as a "heart hickie").

Therefore, what is needed is a device and method of isolating a surgical site for cardiac and cardiovascular surgery. The device should contact a minimal surface of the heart, accommodate the non-planar geometry of the heart, grip the heart firmly, yet gently, and should be easy to apply to and to remove from a beating heart.

Blood in arteries can spew out from the anastomosis site during surgery, which reduces visualization for the surgeon. Periodically, blood must be manually removed by an assistant typically with a blower. The surgeon, therefore, must stop the procedure so that blood can be removed. What is needed, therefore, is a stabilization device integral with a blower device so that the blower could be operated remotely without interfering with the procedure.

SUMMARY OF THE INVENTION

A device and method is provided for isolating a heart surface, particularly, the surface of a beating heart during cardiovascular surgery. The device utilizes rotation to attach to the heart surface and then spread the heart which isolates the spread portion of the heart for surgery.

Disclosed is a device for isolating a cardiac surgical site. The device generally comprises a first finger (which may be cylindrical) having a clinging accessory for attaching the first finger to a heart. Furthermore the device could comprise a second finger having a clinging accessory for attaching the second finger to the heart, a first joint disposed on the first finger so that the first finger may rotate on a surface of the heart such that said rotation stretches a surgical site, and a link for attaching the first finger to the second finger. In addition, a first stopper may be disposed on the first finger for preventing undesired rotation of the first finger to isolate the surgical site.

The accessory for attaching could comprise a plurality of tines, a plurality of suction points, or a rough textured surface such as a surface similar to sandpaper, for example. In addition, the first joint or a second joint (disposed on the second finger) could comprise a rotatable handle coupled in a sleeve. Furthermore, the first stopper or a second stopper (disposed on the second finger) could be configured such that the rotatable handle comprises at least one notch and the sleeve has at least one rib. Likewise, the first stopper or the second stopper (disposed on the second finger) could be configured such that the rotatable handle comprises at least one rib and the sleeve has at least one notch. The handle could comprise an O-ring groove for securing an O-ring about an end of the handle.

The link could comprise a ball and socket joint disposed between the first finger and the second finger for providing multi-axis articulation of the first finger and the second finger, as well as a first attachment bar coupled between the first handle and the ball and socket joint, and a second attachment bar coupled between the second handle and the ball and socket joint. Conversely, the link could comprise a first ball and socket joint associated with the first handle, a second ball and socket joint associated with the second handle, and an attachment bar for coupling the first ball and socket joint to the second ball and socket joint.

More generally, the present invention provides a means is provided for isolating a cardiac surgical site. The means for isolating comprises a first support means, such as a finger or a functional equivalent, having a clinging means for attaching the first support means to a heart, and a second support means, such as a second finger or a functional equivalent, having a clinging means for attaching the second support means to the heart. The means for isolating also includes a rotating means, such as a cylinder or a functional equivalent, disposed on the first support means so that the first support means may rotate on a surface of the heart, a locking means, such as a rib and notch, or a functional equivalent, disposed on the first support means for preventing undesired rotation of the first support means. An attaching means, such as a link or a functional equivalent, connects the first support means to the second support means.

There is also provided a shield or guard attached to the fingers so the clinging means will not catch sutures, gloves or tissues during the medical procedure. The shield may also have a sprayer for washing the surgical site.

In another embodiment, a method of isolating a cardiac surgical site is provided. The method comprises disposing a first finger on a heart, clinging the first finger to the heart surface, disposing a second finger on a heart, clinging the second finger to the heart surface, and rotating the first finger for achieving selective isolation of cardiac tissue. The method may further comprise rotating the second finger, locking the first finger to prevent rotation, or locking the second finger to prevent rotation. The method may also provide that clinging comprises penetrating the surface of the heart, applying suction to the surface of the heart, or applying an abrasive surface for frictionally gripping the surface of the heart. In addition, when applying a finger, the method may further comprise the step of compressing the finger onto the heart surface. Furthermore, the method could include the step of elevating the finger while maintaining its attachment to the heart surface.

The rotational action allows the physician to overcome problems associated with fatty tissue on the heart surface, to adjust the spread of the heart surface during surgery, and to attach and detach from the heart quickly.

BRIEF DESCRIPTION OF THE DRAWINGS

Other aspects of the invention, including specific embodiments, are understood by reference to the following detailed description taken in conjunction with the drawings in which:

FIG. 2 shows a side view of the device shown in FIG. 1;

FIG. 3 is an exploded view of one arm of the device of FIG. 1;

FIG. 4 is a front view of the finger having tines attached to the holes;

FIG. 5 is a cut rear view of the handle taken along line 5—5 of FIG. 3;

FIG. 6 shows the sleeve in greater detail;

FIG. 7 is a cut side view of an arm in a locking position where the locking position is defined as the position of the device when the rib is set in a notch;

FIG. 8 illustrates the sleeve relative to the handle when the device is in a rotatable position;

FIG. 9 is a flow diagram of one method;

FIG. 10 is an isometric drawing of the present invention which includes a flexible arm assembly;

FIG. 11 is a side view of another embodiment;

FIG. 11*b* is an isometric drawing of the embodiment shown in FIG. 11*a*;

FIG. 11*c* is a front view of the embodiment shown in FIG. 11*a*;

FIG. 12*a* is a side view of another embodiment;

FIG. 12b is an isometric drawing of the embodiment shown in FIG. 12a;

FIG. 13a is a side view of another embodiment;

FIG. 13b is a portion of a front view of the embodiment shown in FIG. 13a;

FIG. 14a is a side view of another embodiment;

FIG. 14b is an exploded view of FIG. 14a;

FIG. 14c is a section view of the embodiment shown in FIG. 14a;

FIG. 16a is an isometric drawing of one embodiment of the present invention;

FIG. 16b is an exploded isometric view of FIG. 16a;

FIG. 16c is another isometric drawing of the embodiment shown in FIG. 16a;

FIG. 16d is an exploded isometric view of FIG. 16a;

References in the detailed description correspond to like references in the figures unless otherwise indicated.

DETAILED DESCRIPTION

The present invention provides devices and methods for isolating a heart surface, and particularly the surface of a beating heart, during cardiovascular surgery. The device attaches to the heart surface and then utilizes rotation to spread the heart and isolate the spread portion of the heart (surgical site) for surgery. The rotational action allows the physician to overcome problems associated with fatty tissue on the heart surface to adjust the spread of and tension on the surgical site during surgery, and to attach and detach the device from the heart quickly. Other advantages and uses of the present invention will be apparent to those of ordinary skill in the art from the following description of the drawings.

Figures 1, 1A:
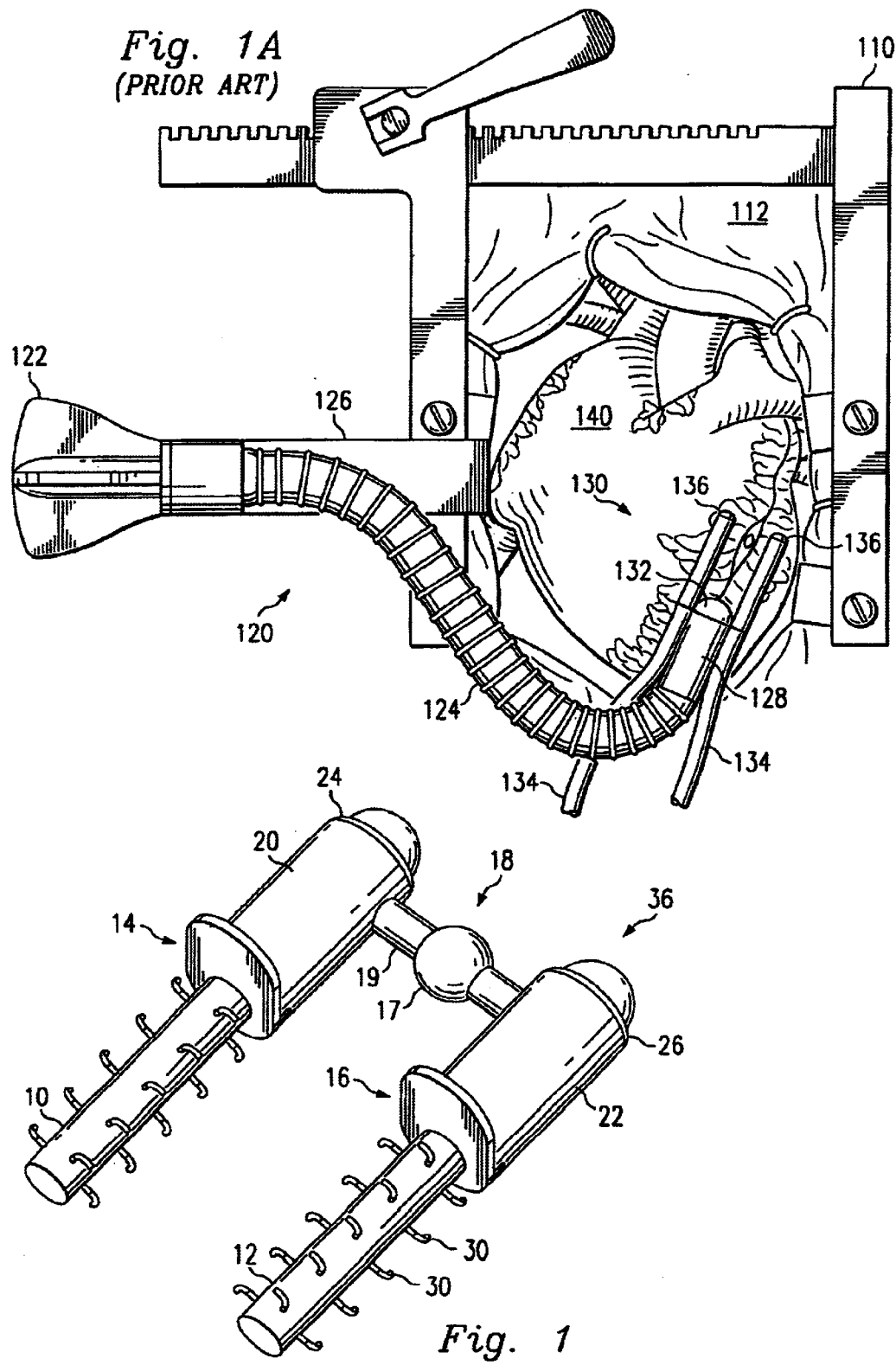
FIG. 1A (prior art) shows a cardiac immobilization device attached to a heart surface.
FIG. 1 is an isometric view of one embodiment of a device.

FIG. 1 is an isometric view of one embodiment of a device. The device generally comprises a pair of stainless steel fingers 10, 12 which are mounted in stainless steel handles 14, 16. Of course, the fingers 10, 12 and the handles 14, 16 may be made of any other material, such as plastics, rubber, other metals, or composite materials, for example. Furthermore, the fingers 10, 12 and the handles 14, 16 could be formed, cut or molded as a single unit. Stainless steel sleeves 20, 22 fit over the handles 14, 16 and are held in place about the handles 14, 16 by resilient O-rings 24, 26. Of course, sleeves 20, 22 could be made out of any material, including plastic, nylon, or rubber. The combination of a finger, a handle, a sleeve, and an O-ring is called an "arm." To couple two arms together, the sleeves, 20, 22 are attached together by a link 18 which is shown in FIG. 1 as a ball and socket assembly, for example the combination of both arms and link 18 is known as a finger assembly 36.

A link is any device or collection of devices used to associate a finger and a stabilization device, such as another finger. The link 18 of FIG. 1 comprises a stainless steel ball 17, which is weldedly coupled to each sleeve 20, 22 by stainless steel attachment bars 19. The ball 17 is securely fastened in a socket 128 of the flexible arm assembly 120 shown in FIG. 1a. Of course, other link devices may be used. For example, the link 18 could comprise an attachment bar alone. Furthermore, ball 17 could be made out of plastic or nylon and molded as a single unit to attachment bars 19. Likewise, stabilizing members may have a variety of designs, and these other designs may use other types of mechanical links to maintain a predetermined distance between the fingers.

FIG. 2 shows a side view of the device illustrated in FIG. 1. Finger 10 has a plurality of tines 30 which function as a clinging accessory to attach the device to a heart surface. Accordingly, a clinging accessory provides a finger traction to a heart surface. Other clinging accessories (such as suction holes, suction cups, rough textured surfaces (such as sandpaper), barbs, or electrostatic attachment, for example) are well known in the art and may be adapted for use. Also, the handle 14 has a knob 42 which extends higher than the sleeve 20 so that the physician may grasp and rotate the handle 14. The sleeve 20 has a plurality of notches 50, and the handle 14 has a rib 40 which fits securely inside of one notch 50. Accordingly, the combination of the rib 40 and a notch 50 together form a stopper which may be set to prevent rotation of the fingers 10, 12 as discussed below. A better understanding of the form and function may be gained by examining the devices' individual components and their interrelations.

FIG. 3 is an exploded view of one arm of the device of FIG. 1. In FIG. 3, the finger 10 is seen to possess a plurality of holes 32 which accept the tines 30. Although five holes 32 and five tines 30 are shown in FIG. 3, it should be understood that the finger 10 may have any number of holes 32 and a corresponding number of tines 30. The holes 32 are of sufficient depth so that the tines 30 may be attached therein with solder, glue or by other means. Although the finger 10 of FIG. 3 is shown to be cylindrical, it should be understood that a finger may have any geometry so long as it may attach to a heart surface and stretch a surgical site by rotating. Finger 10 also has an attachable portion 34 which fits securely in a cylinder 44 of the handle 14.

The handle 14 has a grippable knob 42 which is capable of being securely grasped and turned. Abutting the grippable knob 42 is the rib 40. At the other end of the handle 14 is a groove 48 which functions as an O-ring seat. The end of the handle 14 having the groove 48 is preferably shaped like a hemisphere to facilitate placing the O-ring 24 onto the groove 48.

FIG. 4 is a front view of the finger 10 having tines 30 attached and holes 32. From FIG. 4 it is seen that the tines 30 have a hook shape which minimizes heart surface penetration and which facilitates the release of the tines from the heart muscle. The tines are of a stiffness so that should a stretching rotation require the releasing of the tines from the heart surface, they may release without ripping the heart surface, and then re-penetrate the heart surface at a new location, if necessary. Also, it should be noted that the tines point generally in the direction of the grabbing rotation. Although four linear rows are shown in FIG. 4, the invention may have any number of rows which may include nonlinear, or even apparently random, row formations. In one embodiment, the tines have a length of about one quarter inch. Of course, other methods of attachment are well known in the art. These include but are not limited to, rough textured surfaces such as sandpaper, barbs, electro-statics, and suction holes, for example.

FIG. 5 is a cut rear view of the handle 14 taken along line 5—5 of FIG. 3.

From this view it can be seen that the grippable knob 42 extends both above and below the cylinder 44. The portion of the grippable knob 42 extending below the cylinder 44 forms a lip 46 which is of a width that matches the circumference of the sleeve 20 such that when the sleeve 20 fits over the cylinder 44 the outside of the lip 46 aligns with the outside of the sleeve 20. This view also illustrates that the rib 40 is of a width and size to accommodate the notch 50.

FIG. 6 shows the sleeve 20 in greater detail. As shown, sleeve 20 has a plurality of notches 50. Although four notches are shown in FIG. 6, the sleeve 20 may have any number of notches 50 so that the rotation of the fingers may be held at varying degrees of rotation. In addition, one side of the sleeve 20 has a hole 54, or other surface preparation, for accepting the attachment bar 19 (of course, the sleeve 20 may have other apertures attached to it depending on the link 18 used; likewise, the sleeve 20 may be connected to a link via welding, which avoids the need for apertures or modifications). The O-ring 24 pushes against the handle 14 so as to apply tension to the sleeve 20 to securely force a rib 40 over notch 50, as described below. Accordingly, the sleeve 20 has a cylinder 56 which at the end opposite the notches 50 has a tapered lip 52 which is shaped to accept the O-ring 24 to minimize wear on the O-ring 24.

FIG. 7 is a cut side view of an arm in a locking position where the locking position is defined as the position of the device when the rib 40 is set in a notch 50. Also, when in the locking position, the sleeve 20 fits securely against the handle 14. In the locking position, the O-ring 24 in groove 48 exerts a force upon the sleeve 20 to keep it in place abutting the handle 14. Furthermore, note that the rib 40 also abuts the sleeve 20, indicating that a notch 50 (not shown) is in position about the rib 40, forming a stopper.

FIG. 8 illustrates the sleeve 20 relative to the handle 14 when the device is in a rotatable position. Here, it can be seen that the sleeve 20 is pushed against the O-ring 24, causing distortion of the O-ring 24. The separation of the sleeve 20 from the grippable knob 42 removes the notch 50 from the rib 40 and allows for the handle 14 to be rotated. Accordingly, as the handle 14 rotates so does the finger 10. Then, depending on the direction of the rotation, the heart surface will either be stretched or compressed. A three dimensional drawing of the present invention is illustrated in FIG. 10 in which finger assembly 36 (FIG. 1) is mounted on a flexible arm assembly 190. Flexible arm assembly 190 includes a flex arm 191 which may be bent and twisted into various shapes to access different locations on the heart surface. Socket 192 is on one end of flexible arm 191. Socket 192 has a spherical void (not shown) which allows it to mate with ball 17 (FIG. 1). At the other end of flex arm 191 is universal retractor mounting 194 and variable tension lock 195. Universal retractor mounting 194 mounts to chest retractor 110 (FIG. 1a). Variable tension lock 195 tightens a cable (not shown) within flex arm 191. This tightening causes flexible arm 191 to become rigid and immobile, and thus allows fingers 10 and 12 remain placed against the heart after placement.

One method of implementation uses the above disclosed device. Accordingly, FIG. 9 is a flow diagram of one embodiment of a method First, the chest cavity is cut and opened and held securely in place, typically by a chest retractor, in an expose heart and place retractor step 90. As advances in open heart surgery are made, less intrusive means of exposing the heart for surgery will be developed and this method should in no way be read to limit its use to open chest cavities, or in the use of retractors.

Following the securing of the chest retractor, flex arm 191 with a finger 10 attached thereto (FIG. 10) is attached to the retractor in a fix flex arm step 91. Next, finger 10 is placed about the area of the heart on which surgery is to be performed in a finger placement step 92. Then, the finger 10 is attached to the heart in a finger attachment step 94 and in a make flex arm rigid step 95, the flex arm is made stiff, typically by tightening variable tension lock 195 (FIG. 10).

The fingers 10, 12 may be placed together on the heart in a single finger placement step 92 and then attached to the heart in a single finger attachment step 94, or each finger 10, 12 may be placed on the heart surface, and then attached to the heart surface independently of each other. In any event, the result is that the finger 10 lies on one side of the surgical site, and a second finger 12 lies generally on the opposite side of the surgical site. Optionally, to achieve better traction in a following rotation step, and thus better isolation of the heart surface, the fingers 10, 12 may be gently pressed onto the heart (the fingers do not penetrate the heart surface).

Next, in a finger rotation step 96, at least one finger is rotated in a direction which increases the surface tension of the heart surface across the surgical site until a desired tension is achieved across the surgical site area. Once the desired tension is achieved on the heart surface, the tension is maintained by locking the device in that current state of rotation in a position locking step 98. Yet even better heart surface isolation may be achieved at this point by lifting the fingers 10, 12 (and thus the isolated heart surface) slightly. Surgery may then be performed at the isolated surgical site on the heart as well as on any veins or arteries going to or from the surgical site. If necessary, during surgery, the handles may be rotated in either a gripping or releasing direction to increase or decrease the tension at the surgical site. Then, after the surgery is completed, the above detailed steps may be reversed and the device removed.

FIGS. 11–17 describe various examples and embodiments. For brevity and clarity, a description of those parts which are identical or similar to those described in connection with other embodiments illustrated in FIGS. 1 through 10 will not be repeated. Reference should be made to the foregoing paragraphs with the following description to arrive at a complete understanding of these embodiments. It is understood that features of various examples and embodiments may be interchanged, combined or otherwise reconfigured.

FIG. 11a is a side view of finger assembly 201. In FIG. 11a, finger 210 is hidden from view by finger 212. Fingers 210 and 212 are similar to fingers 10 and 12 (FIG. 1), except that fingers 210 and 212 are cylindrically convex or have a convex cylindrical shape. "Cylindrically convex" means that the diameter of fingers 210 and 212 at end 202 is approximately the same as the diameter at end 204, but the diameter of fingers 210 and 212 gradually increases from end 202, at point B, to a maximum diameter at point A (FIG. 11a). Point A is approximately at the longitudinal midpoint between end 202 and 204. The diameter of fingers 210 and 212 at point A is typically twice the diameter of fingers 210 and 212 at point B. However, the diameter of fingers 210 and 212 at point A could be any multiple of the diameter at point B. Thus, fingers 210 and 212 can be said to be cylindrically convex.

FIG. 11b is an isometric drawing of finger assembly 201 showing fingers 210 and 212 adjacent to the surgical site. In FIG. 11b, finger 210 is placed on one side of the surgical site 206 and finger 212 is placed on the other side of surgical site 206. In a method described previously in reference to an earlier embodiment, fingers 210 and 212 may be rotated in a direction which increases the surface tension of the heart surface across the surgical site. The direction and relative magnitude of the surface tension after fingers 210 and 212 is rotated can be represented as arrows 220 through 238 in FIG. 11b. As can be seen in FIG. 11b, arrows 224 and 234, which are approximately at the longitudinal midpoint of fingers 210 and 212, are significantly longer than arrows 220, 228, 230, and 238 which represent the relative surface tension are at the ends of fingers 210 and 212. Thus, the surface tension in the middle of the site is greater than at the edges. This increase in surface tension at the center of the surgical site is due to the fact that a portion of finger 210 at the midpoint must travel a greater distance than the portion of finger 210 at ends 202 or 204 for the same amount of angular rotation.

This concept is illustrated in FIG. 11c, which is a front view of finger 212. Point B is a point at end 202 on the outer circumference of finger 212. Point A is also on the outer circumference of finger 212, but close to the longitudinal midpoint of finger 212 (FIG. 11a). As illustrated in FIG. 11c, when finger 212 is rotated about its longitudinal axis through an angle a, point B moves to point B'. Similarly, point A moves to A'. Point A moves more than point B. In fact, the greater the relative diameter of the circumferences, the greater the relative movement between point A and point B along their respective circumferences. This increase in movement causes a corresponding increase in surface tension. Thus, the surgeon can increase the surface tension in the middle of the surgical site (FIG. 11b).

FIG. 12a is a side view of finger assembly 201, however, in this embodiment the finger elements are replaced with fingers 310 and 312. In FIG. 12a, finger 310 is hidden from view by finger 312. Fingers 310 and 312 are similar to fingers 10 and 12, except that fingers 310 and 312 are cylindrically concave or have a concave cylindrical shape. "Cylindrically concave" means that the diameter of fingers 310 and 312 at end 302 is approximately the same as the diameter at end 304, but the diameter of fingers 310 and 312 gradually decreases from end 302, at point C, to a minimum diameter at point D. Point D is approximately at the longitudinal midpoint between end 302 and 304. The diameter of the fingers at point C could be any multiple of the diameter at point D, depending on the amount of relative surface tension desired and the material used.

FIG. 12b is an isometric drawing of finger assembly 201 showing fingers 310 and 312 adjacent to the surgical site. In FIG. 12b, finger 310 is placed on one side of the surgical site 206 and finger 312 is placed on the other side of surgical site 206. In a procedure similar to the one described in the first embodiment, fingers 310 and 312 are rotated in a direction which increases the surface tension of the heart surface across the surgical site. The direction and relative magnitude of the surface tension of the heart surface is represented in FIG. 12b as arrows 320 through 338. As can be seen in FIG. 12b, arrows 324 and 334, which are approximately at the longitudinal midpoint of fingers 310 and 312, are significantly shorter than arrows 320, 328, 330, and 338 which represent the surface tension at the ends of fingers 310 and 312. This decrease in surface tension at the center is due to fact that the portion of finger 310 at the longitudinal midpoint travels a shorter distance than the portion at ends 302 or 304 for the same amount of angular rotation. The surgeon, therefore, can thus decrease the surface tension in the middle of the surgical site relative to the outside area of the surgical site.

FIG. 13a is a side view of a finger assembly, however, in this embodiment the finger elements are replaced with fingers 410 and 412. Fingers 410 and 412 have a camber on one side to form a cam shaped cross-section. Fingers 410 and 412 are cylindrically cam-shaped, which means that the diameter of fingers 410 and 412 at end 402 is approximately the same as the diameter at end 404, but the diameter of fingers 410 and 412 gradually increases eccentrically from end 402, at point E, to a maximum diameter at point F. Point F is approximately at the longitudinal midpoint between end 402 and 404.

FIG. 13b is a front view of finger 412. In this view, end 402 is shown as circle 406. Outline 408 represents the cross-sectional outline of finger 412 at approximately point F (FIG. 13a). As illustrated in FIG. 13b, the cross-sectional shape of finger 412 is that of an eccentric cam.

This embodiment allows the amount of surface tension to be vary, depending on the circumstances and the surgeon's preferences. If the surgeon feels that greater tension across the middle of surgical site is important, the surgeon can position fingers 410 and 412 with camber side 414 down facing the heart's surface. On the other hand, if the surgeon desires a more uniform amount of tension across the entire surgical site, the surgeon can keep camber side 414 up, away from the heart.

As explained previously, there are several disadvantages associated with using suction to isolate a surgical site. Regardless of the disadvantages, many surgeons may prefer to use suction to stabilize the heart. One of the primary disadvantages with using suction is that the horizontal surface tension of the heart must be maintained by a vertical suction force. As explained previously, there are disadvantages with using only a vertical suction force maintain a horizontal surface tension.

This embodiment overcomes many of the limitations of the prior art because it addition to the vertical suction force, this embodiment also increases the surface tension by using a horizontal rotating force.

Turning now to FIG. 14a, which is a side view of an embodiment which uses suction to attach the finger elements to the surface of the heart. Because this is a side view, finger 1410 is hidden from view by finger 1412. In this embodiment, finger 1412 is partially surrounded by a cylindrical cover 1418.

FIG. 14b is an exploded view of FIG. 14a. Finger 1412 is a hollow cylinder which has a plurality of longitudinal slits 1414 around its perimeter. Finger 1412 also has attachable portion 1434 which, similar to the first embodiment, fits securely in cylinder 1444 of the handle 1415. However, in this embodiment attachable portion 1434 is hollow and has connection 1420 at one end. Vacuum tube 1422 fits tightly over connection 1420 such that a hermetic seal is created between vacuum tube 1422 and connection 1420. Similar to previous embodiments, sleeve 20 fits over cylinder 1444 and is restrained by O-ring 24.

Figure 14C:
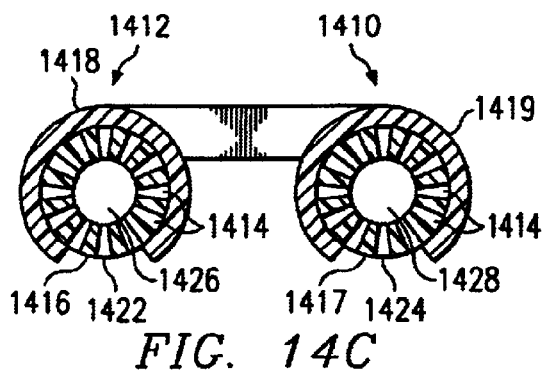

FIG. 14c is a section view through fingers 1410 and 1412. Fingers 1410 and 1412 have hollow cylindrical openings 1426 and 1428 running longitudinally through their respective centers. Slits 1414 form a plurality of ribs 1416 and 1417 within the perimeter walls of fingers 1410 and 1412. Of course, slits 1414 could be a variety of shapes. Also shown in FIG. 14c, are covers 1418 and 1419 which partially surrounds fingers 1410 and 1412. Each of covers 1418 and 1419 have a single large slit 1423 and 1424. Fingers 1410 and 1412 rotate within and relative to covers 1418 and 1419.

Figure 14D:
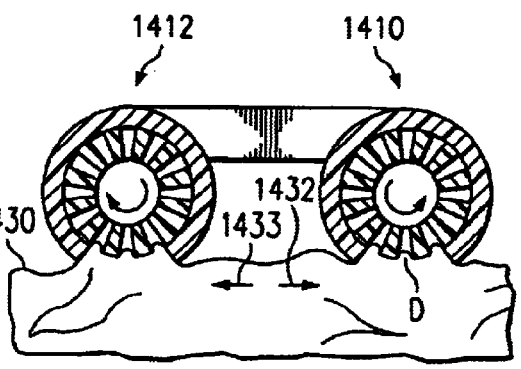
FIG. 14d is a section view of the embodiment shown in FIG. 14a adjacent to the surface of a heart.

FIG. 14d is a section view of fingers 1410 & 1412 adjacent to the surface of a heart. In operation, a vacuum pump or source (not shown) is attached to vacuum tube 1422 (FIG. 14b) which creates a low pressure or suction in vacuum tube 1422. This low pressure is transferred through the hollow portion of attachment portion 1434 to cylindrical openings 1426 and 1428. The low pressure causes a suction force in slits 1414 which allow fingers 1410 and 1412 to attach to heart surface 1430 through suction as shown in FIG. 14d. Finger 1410 can then be rotated with respect to finger 1412 and vice versa. This rotation causes a horizontal surface tension or stretching in the direction represented by arrows 1433 and 1432, and thus the surgical site can be stabilized by a lateral force—not a vertical force as in the prior art.

Various clinging accessories may be used to attach fingers 10, 12, 210, 212, 310, 312, 410, and 412 to the surface tissue of the heart. The clinging accessory previously shown uses plurality of tines 30 in FIGS. 1–4, 7–8, 11–13. As previously discussed, tines 30 are only one form of a variety of clinging accessories that could be used with any form of the previous embodiments. Other clinging accessories (such as suction holes, suction cups, rough textured surfaces (such as sandpaper), barbs, or electrostatic attachment, for example) may be used with any embodiment. It is understood that as fingers are gently pressed against the heart, they do not penetrate the heart surface but instead engage the surface in a manner that enables manipulation of tissue without tissue damage.

Figure 15A:
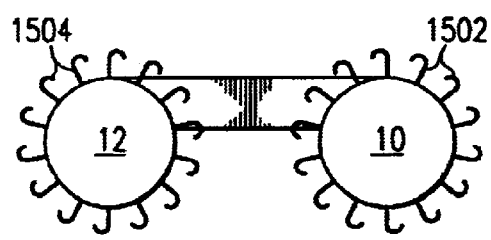
FIG. 15a is a front view of the fingers 10 and 12 (FIG. 2) with another embodiment of a clinging accessory.

Nylon or other forms of plastic tines, for instance, may be less traumatic to the heart tissue than the use of stainless steel or tungsten carbide tines. FIG. 15a is a front view of an embodiment of a finger assembly with the fingers 10 and 12 (FIG. 2), however finger 10 is surrounded by a plurality of nylon hooks 1502 and finger 12 is surround by a plurality of nylon hooks 1504, hooks 1502 and 1504 are similar to that used in a Velcro™ fastening system. Hooks 1502 and 1504 are approximately 0.050 inches in length. Hooks 1502 and 1504 are designed to minimize heart surface engagement. The hooks are of a stiffness so that should a stretching rotation require the releasing of the tines from the heart surface, they may release without ripping the heart surface, and then engage the heart surface at a new location, if necessary. Also, it should be noted that the tines point generally in the direction of the grabbing rotation.

Figure 15B:
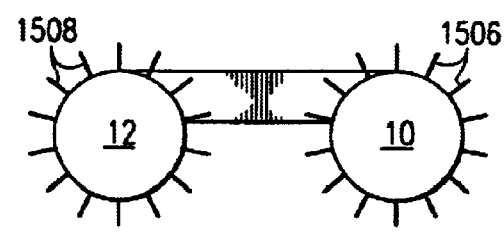
FIG. 15b is a front view of the device shown in FIG. 2 with another embodiment of a clinging accessory.

Another embodiment of clinging accessory is illustrated in FIG. 15b, which employs a plurality of straight nylon tines or bristles 1508 surrounding finger 12 and nylon bristles 1506 surrounding finger 10. Bristles 1506 and 1508 gently engage into the heart tissue. Of course, bristles 1506 could also be made out of any type of plastic or stainless steel.

Figure 15C:
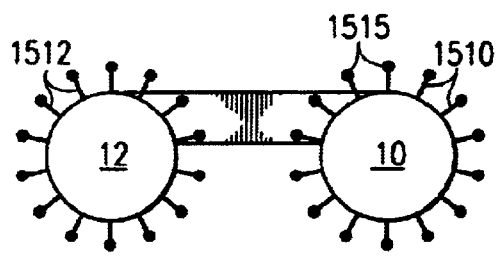
FIG. 15c is a front view of the device shown in FIG. 2 with another embodiment of a clinging accessory.

FIG. 15c is a front view of fingers 10 and 12 where the finger elements are surrounded by a plurality of nylon tines or bristles 1510 and 1512, respectively. In this embodiment, bristles 1510 and 1512 have tiny balls or spheres 1515 at the protruding end of the bristles. The diameter of the balls are larger than the diameter of the bristles. These different embodiments have unique advantages and disadvantages and offer the surgeon more choices based on personal preferences. For instance, bristles 1508 and 1506 offer better traction than bristles 1510 and 1512. However, bristles 1510 and 1512 reduce trauma to the heart tissue.

Figure 15D:
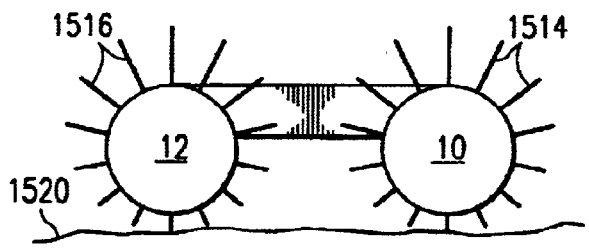
FIG. 15d is a front view of the device shown in FIG. 2 with another embodiment of a clinging accessory.
Figure 15E:
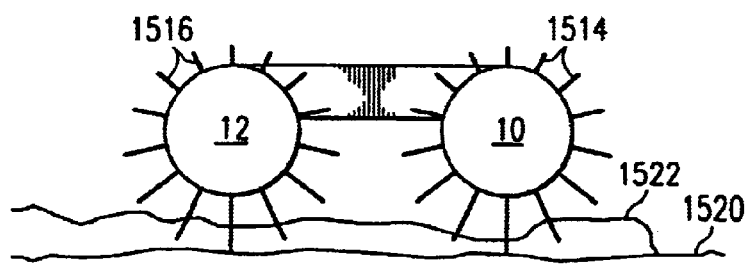
FIG. 15e is a front view of the device shown in FIG. 2 with another embodiment of a clinging accessory.

FIG. 15d is a cross section view of fingers 10 and 12 adjacent to heart tissue 1520. In this embodiment, a plurality of straight nylon bristles 1516 and 1514 are used as the clinging accessory, however bristles 1516 and 1514 use bristles of a progressively different degree of length. As illustrated in FIG. 15d, bristles 1516 and 1514 are longer on the top side of fingers 10 and 12 than the bristles on the bottom side. The length of each radial row of bristles vary according to the radial or angular position of each row at the perimeter of the surface of the finger. As shown in FIG. 15d, the shorter bristles are pointed towards heart tissue 1520. Similarly, FIG. 15e is a cross section view of fingers 10 and 12 adjacent to fat tissue 1522 and heart tissue 1520. In this figure, the longer bristles of bristles 1516 and 1514 pointed down towards the heart tissue. This embodiment provides the surgeon with the option of varying the degree of engagement into the heart or fat tissue.

Depending on the condition and location of the surgical site, heart tissue 1520 may be surround by fat tissue 1522 (FIG. 15e). On the other hand, if little or no fat tissue surrounds the surgical site, the surgeon can simple rotate fingers 10 and 12 so that the shorter bristles are adjacent to heart tissue 1520, as illustrated in FIG. 15d.

As discussed previously, the finger elements use clinging accessories to "grab" the tissue of the heart. The clinging accessories can be hooks, tines, bristles or other rough surfaces. These clinging accessories may tend to catch and snag sutures used by surgeons during the procedure. To avoid snagging of sutures, gloves, and transplanted arteries, a suture guard may be positioned over the finger elements. Such a device is illustrated in FIG. 16a.

FIG. 16a is an isometric view looking down upon finger assembly 36 as it is attached to suture guard 1602. FIG. 16b is an exploded isometric view of FIG. 16a showing how suture guard 1602 fits between sleeve 20 and 22. Suture guard 1602 can be made of metal, plastic or any other acceptable material. Plastic is the preferred embodiment because it can be molded into intricate shapes easily, is lightweight, and it can be clear. Using clear plastic allows the surgeon to see through suture guard 1602, which allows the surgeon to see as much of the surgical site as possible. FIG. 16c is an isometric view looking up at the bottom of finger assembly 36 when it is attached to suture guard 1602. FIG. 16d is an exploded view of FIG. 16c.

Turning now to FIG. 16d, the suture guard 1602 has fins 1604 through 1609 which are shaped to press against the outside perimeter surface of the sleeves 20 and 22. This dual pressure against the sleeves 20 and 22 restrains the suture guard 1602 and prevents the suture guard 1602 from slipping off the sleeves 20 and 22. The suture guard 1602 also has a plurality of elements or legs 1612 and 1614, which cantilever over fingers 10 and 12 to protect any sutures from tines 30. The legs 1612 and 1614 are generally parallel or longitudinally aligned with the fingers 10 and 12. In this embodiment, the legs 1612 and 1614 have a cross-sectional shape of an arc. An arc cross-sectional shape allows the legs to closely follow the contours of the fingers 12 and 10 while minimizing any visual obstruction to the surgical site. The legs 1612 and 1614 are attached and supported by the fins 1608 and 1609 which are attached to a connecting member 1610. Connecting member 1610 connects the fins 1608, 1606, and 1604, and thus, distributes and transfers any force from the cantilevered die-legs 1612 and 1614 to the fins 1606 and 1604.

Figure 17A:
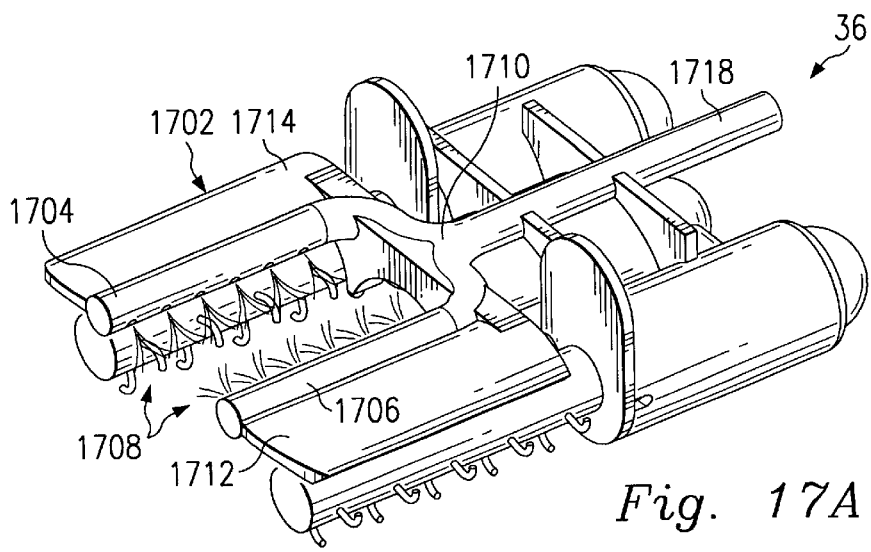
FIG. 17a is an isometric drawing of another embodiment.

FIG. 17*a* is an isometric drawing of finger assembly 36 attached to an embodiment of the suture guard with a blower. In this embodiment, suture guard 1702 has spray tubes 1704 and 1706 along the inside edge of the legs 1712 and 1714. The spray tubes 1704 and 1706 have a plurality of openings or nozzles 1708. The spray tubes 1704 and 1706 may be independent of legs 1712 or 1714 or they may be molded together, and thus become integral with legs 1712 and 1714. In another embodiment, the legs 1712 and 1714 could simply be hollow and have a plurality of nozzles along the inside edge.

Spray tubes 1704 and 1706 are hermetically joined with y-connection 1710 to pressure tube 1718. Pressure tube 1718 is a flexible plastic or rubber tube capable of delivering a pressurized fluid from a supply of saline solution, water, air and/or carbon dioxide (FIG. 17*b*) to spray tubes 1704 and 1706. The pressurized fluid exits through nozzles 1708. Nozzles 1708 are positioned, or "aimed" at the surgical site such that when a fluid flows through them, a plurality of sprays are created which washes the surgical site.

Figure 17B:
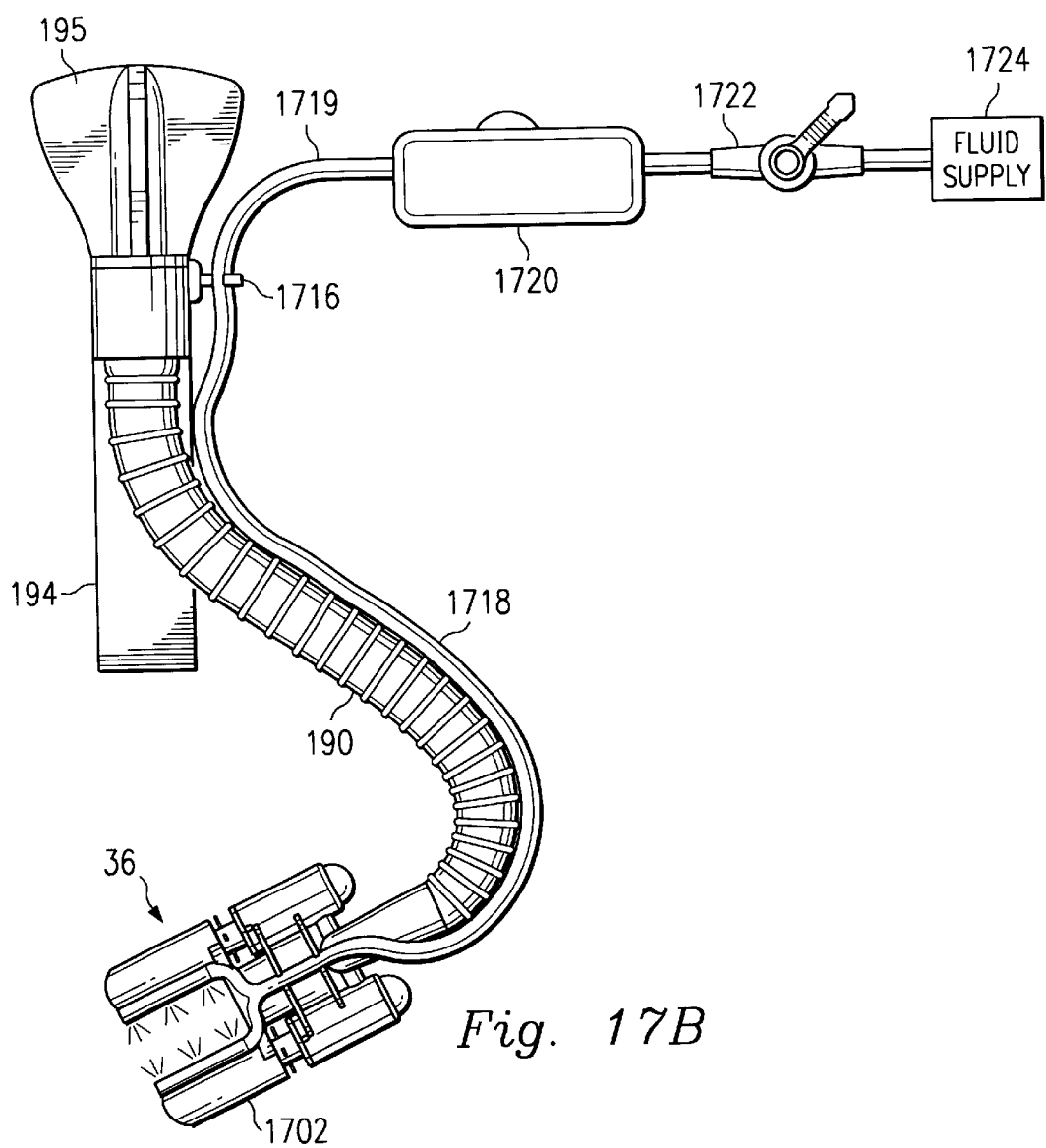
FIG. 17b is a combination top view and schematic view of another embodiment present invention.

FIG. 17*b* is a combination top view and schematic view of suture guard 1702 attached to finger assembly 36. Finger assembly 36 is mounted on a flexible arm assembly 190, which includes a universal retractor mounting 194 and variable tension lock 195. As discussed previously, universal retractor mounting 194 mounts to chest retractor 110 (FIG. 1*a*). Pressured tube 1718 is shown running alongside of flexible arm assembly 190. It is important to note, that in another embodiment, pressured tube 1718 could also be incorporated into flexible arm assembly 190. Attachment connection 1716 is either attached to or integral with universal retractor mounting 194. Attachment connection 1716 connects pressurized tube 1718 with attachment tube 1719. Attachment tube 1719 is connected to water/air supply 1724. Between water/air supply 1724 and attachment connection 1716 is stop lock 1722 and metering valve 1720, all fluidly connected via attachment tube 1719.

Water/air supply 1724, known in the art, can be a saline bag combined with a gas source, such as carbon dioxide or air. The gas in the source is kept under pressure. Furthermore, there is a certain amount of head pressure in the saline if the saline is hangs above the surgical site. This combined pressure causes the fluid, which is a combination of gas and saline to flow through attachment tube 1719. Stop lock 1722 cuts off the fluid in the event that metering valve 1720 cannot control the flow of fluid through attachment tube 1719. Under normal circumstances, however, metering valve 1720 controls the flow of fluid through pressured tube 1718, and ultimately, to nozzles 1708 (FIG. 17*a*). Metering valve 1720 is a roller clamp valve and is well known in the art.

The fluid continues to move through attachment tube 1719 to pressured tube 1718. Pressured tube 1718 joins spray tubes 1704 and 1706 and v-connector 1710 (FIG. 17*a*). As previously discussed, the fluid then moves through spray tubes 1704 and 1706, out nozzles 1708 in the form of a fine spray (FIG. 17*a*). The fine spray washes the surgical site.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications.

What is claimed is:

1. A device for isolating a cardiac surgical site, comprising:
    a first and second finger, each finger having a clinging accessory adapted to attach to a heart, wherein at least one of the fingers may rotate on a surface of the heart such that the rotation stretches a surgical site, and at least one of the fingers has a varying diameter; and
    a link coupling the first finger to the second finger, and a stabilizing member coupling to the link, wherein the link comprises:
        a ball disposed between the first finger and the second finger adapted to secure an attachment to the stabilizing member;
        a first attachment bar coupled between the first finger and the ball; and
        a second attachment bar coupled between the second finger and the ball.

2. The device of claim 1, wherein the clinging accessory comprises a plurality of tines, each tine having a distal end and proximal end such that the proximal end is coupled to a surface of the finger.

3. The device of claim 2, wherein the distal end is hook shaped.

4. The device of claim 2 wherein the tines are straight.

5. The device of claim 2 wherein the distal end has an enlarged spherical head.

6. The device of claim 1, further comprising a guard coupled to the first finger and the second finger, wherein the guard has at least one element, and wherein the element is longitudinally aligned with at least one finger such that the element partially covers the finger.

7. The device of claim 6, further comprising a spray tube coupled to the guard, wherein the spray tube comprises at least one spray nozzle positioned and directed so that fluids may be sprayed onto a surgical site.

8. The device of claim 7, further comprising a fluid supply controller coupled to the spray tube to regulate a flow of fluids.

9. A device for isolating a cardiac surgical site, comprising:
    first and second finger, each finger having a clinging accessory adapted to attach to a heart, wherein at least one of the fingers may rotate on a surface of the heart such that the rotation stretches a surgical site;
    a guard coupled to the first finger and the second finger; and
    a link coupling the first finger to the second finger, and a stabilizing member coupling to the link, wherein the link comprises:
        a ball disposed between the first finger and the second finger adapted to secure an attachment to the stabilizing member;
        a first attachment bar coupled between the first finger and the ball; and
        a second attachment bar coupled between the second finger and the ball.

10. The device of claim 9, wherein the stabilizing member comprises:
    a socket for coupling with the link;
    a flexible arm with a first end and a second end wherein the first end couples to the socket;
    a tightening device coupled to the flexible arm for fixing the position of the flexible arm; and
    a mounting device coupled to the second end of the flexible arm.

11. The device of claim 9, wherein the guard has at least one element, and wherein the element is longitudinally aligned with at least one finger such that the element partially covers the finger.

12. The device of claim 11, wherein the element has a cross-sectional shape in the form of an arc.

13. The device of claim 11, wherein the guard further comprises a support coupled to at least one element such that at least one element is supported above the respective finger.

14. The device of claim 9, further comprising a spray tube coupled to the guard, wherein the spray tube comprises at least one spray nozzle positioned and directed so that fluids may be sprayed onto a surgical site.

15. The device of claim 14, further comprising a fluid supply controller coupled to the spray tube to regulate a flow of fluids.

16. The device of claim 15, further comprising a supply of fluids coupled to the fluid supply controller, wherein the fluids comprise saline solution.

17. The device of claim 15, further comprising a supply of fluids coupled to the fluid supply controller, wherein the fluids comprise water.

18. The device of claim 15, further comprising a supply of fluids coupled to the fluid supply controller, wherein the fluids comprise carbon dioxide.

19. The device of claim 15, further comprising a supply of fluids coupled to the fluid supply controller, wherein the fluids comprise air.

20. A device for isolating a cardiac surgical site, comprising:

a first and second finger, each finger having a clinging accessory adapted to attach to a heart, wherein at least one of the fingers may rotate on a surface of the heart such that the rotation stretches a surgical site, and at least one of the fingers has a varying diameter; and a guard coupled to the first finger and the second finger.

21. The device of claim 20, wherein the guard comprises an element, and wherein the element is longitudinally aligned with at least one finger such that the element partially covers the finger.

22. The device of claim 21, wherein the element has a cross-sectional shape in the form of an arc.

23. The device of claim 20, further comprising a spray tube coupled to the guard, wherein the spray tube comprises at least one spray nozzle positioned and directed so that fluids may be sprayed onto a surgical site.

24. The device of claim 20, further comprising a fluid supply controller coupled to the spray tube to regulate a flow of fluids.

25. The device of claim comprising a supply of fluids coupled to the fluid supply controller, wherein the supply saline solution.

26. The device of claim 24, comprising a supply of fluids coupled to the fluid supply controller, wherein the supply of fluids comprises water.

27. The device of claim 24, further comprising a supply of fluids coupled to the fluid supply controller, wherein the supply of fluids comprises air.

* * * * *

UNITED STATES PATENT AND TRADEMARK OFFICE
CERTIFICATE OF CORRECTION

PATENT NO. : 6,740,029 B2
DATED : May 25, 2004
INVENTOR(S) : Rogers et al.

It is certified that error appears in the above-identified patent and that said Letters Patent is hereby corrected as shown below:

Item [62], Related U.S. Application Data, please delete "which is a continuation-in-part of application No. 09/376,538, filed on Aug. 18, 1995" and substitute therefor -- which is a continuation-in-part of application No. 09/376,538, filed on Aug. 18, 1999 --.

Signed and Sealed this

Twenty-seventh Day of July, 2004

JON W. DUDAS
*Acting Director of the United States Patent and Trademark Office*